(12) United States Patent
Gross

(10) Patent No.: US 7,811,221 B2
(45) Date of Patent: Oct. 12, 2010

(54) EXTRACARDIAC BLOOD FLOW AMPLIFICATION DEVICE

(76) Inventor: Yossi Gross, 10 HaNotea Street, Moshav Mazor (IL)

( * ) Notice: Subject to any disclaimer, the term of this patent is extended or adjusted under 35 U.S.C. 154(b) by 620 days.

(21) Appl. No.: 11/921,401

(22) PCT Filed: Feb. 10, 2005

(86) PCT No.: PCT/IL2005/000177
§ 371 (c)(1),
(2), (4) Date: Nov. 30, 2007

(87) PCT Pub. No.: WO2005/074384
PCT Pub. Date: Aug. 18, 2005

(65) Prior Publication Data
US 2008/0234537 A1    Sep. 25, 2008

Related U.S. Application Data

(60) Provisional application No. 60/543,700, filed on Feb. 10, 2004.

(51) Int. Cl.
*A61N 1/00* (2006.01)
(52) U.S. Cl. ...................................................... 600/16
(58) Field of Classification Search .................. 600/16; 606/108, 153
See application file for complete search history.

(56) References Cited

U.S. PATENT DOCUMENTS

| | | | |
|---|---|---|---|
| 3,585,983 A | 6/1971 | Kantrowitz et al. |
| 3,866,604 A | 2/1975 | Curless et al. |
| 4,240,409 A | 12/1980 | Robinson et al. |
| 4,527,549 A | 7/1985 | Gabbay |
| 4,583,523 A | 4/1986 | Kleinke et al. |

(Continued)

FOREIGN PATENT DOCUMENTS

EP    1078649    3/2008

(Continued)

OTHER PUBLICATIONS

An Office Action dated Apr. 9, 2009, which issued during the prosecution of Applicant's U.S. Appl. No. 10/546,660.

(Continued)

*Primary Examiner*—George Manuel
*Assistant Examiner*—Shubatra Narayanaswamy
(74) *Attorney, Agent, or Firm*—Martin P. Hoffman

(57) ABSTRACT

Apparatus is provided including first and second chambers, adapted to be in fluid communication with first and second volumes of oxygenated blood of a subject, respectively, the first and second chambers having first and second surfaces, respectively. A third surface is adapted to apply an elastically-derived force, at least a first and second portions of the third surface in mechanical communication with, respectively, the first and second surfaces, during at least a portion of a cardiac cycle. A pressure-sensitive valve is coupled between the first and second chambers, the valve adapted: (a) to be in an open position during at least a portion of systole, such that the first chamber is in fluid communication with the second chamber; and (b) to be in a substantially closed position during diastole, such that the first chamber is substantially not in fluid communication with the second chamber. Other embodiments are also described.

15 Claims, 27 Drawing Sheets

U.S. PATENT DOCUMENTS

| | | | |
|---|---|---|---|
| 4,630,597 | A | 12/1986 | Kantrowitz et al. |
| 4,753,221 | A | 6/1988 | Kensey et al. |
| 4,809,676 | A | 3/1989 | Freeman |
| 4,919,647 | A | 4/1990 | Nash |
| 4,938,766 | A | 7/1990 | Jarvik |
| 5,324,177 | A | 6/1994 | Golding et al. |
| 5,346,476 | A | 9/1994 | Elson |
| 5,514,079 | A | 5/1996 | Dillon |
| 5,554,103 | A | 9/1996 | Zheng et al. |
| 5,749,855 | A | 5/1998 | Reitan |
| 5,928,132 | A | 7/1999 | Leschinsky |
| 5,997,540 | A | 12/1999 | Zheng et al. |
| 6,030,336 | A | 2/2000 | Franchi |
| 6,083,260 | A | 7/2000 | Aboul-Hosn |
| 6,132,363 | A | 10/2000 | Freed et al. |
| 6,168,624 | B1 | 1/2001 | Sudai |
| 6,200,260 | B1 | 3/2001 | Bolling |
| 6,245,007 | B1 | 6/2001 | Bedingham et al. |
| 6,261,304 | B1 * | 7/2001 | Hall et al. ............ 606/194 |
| 6,299,575 | B1 | 10/2001 | Bolling |
| 6,299,637 | B1 | 10/2001 | Shaolian et al. |
| 6,387,037 | B1 | 5/2002 | Bolling et al. |
| 6,390,969 | B1 | 5/2002 | Bolling et al. |
| 6,406,422 | B1 | 6/2002 | Landesberg |
| 6,428,464 | B1 | 8/2002 | Bolling |
| 6,450,942 | B1 | 9/2002 | Lapanshvili et al. |
| 6,511,413 | B2 | 1/2003 | Landesberg |
| 6,572,652 | B2 | 6/2003 | Shaknovich |
| 6,641,610 | B2 * | 11/2003 | Wolf et al. ............ 623/1.3 |
| 6,673,043 | B1 | 1/2004 | Landesberg |
| 6,730,118 | B2 | 5/2004 | Spenser et al. |
| 2002/0103413 | A1 | 8/2002 | Bugg et al. |
| 2002/0151761 | A1 | 10/2002 | Viole et al. |
| 2002/0173693 | A1 | 11/2002 | Landesberg |
| 2002/0173735 | A1 | 11/2002 | Lewis |
| 2003/0127090 | A1 | 7/2003 | Gifford et al. |
| 2003/0135086 | A1 | 7/2003 | Khaw et al. |
| 2004/0097783 | A1 | 5/2004 | Peters et al. |
| 2004/0116769 | A1 | 6/2004 | Jassawalla et al. |
| 2005/0159640 | A1 | 7/2005 | Barbut et al. |
| 2006/0122456 | A1 | 6/2006 | LaRose et al. |
| 2006/0195004 | A1 | 8/2006 | Jarvik |

FOREIGN PATENT DOCUMENTS

| | | |
|---|---|---|
| WO | WO 98/57599 | 12/1998 |
| WO | WO 02/24254 | 3/2002 |

OTHER PUBLICATIONS

U.S. Appl. No. 60/543,700.

Clauses, et al., "Assisted Circulation: 1. The Arterial Counterpulsator", Journal of Thoracic and Cardiovascular Surgery, 41:447, Apr. 1961.

G. Gregoratos, et al., "ACC/AHA/NASPE 2002 Practice Guidelines", JACC vol. 40, No. 9, Nov. 6, 2002, 1703-19.

F. Unger, et al., "The Windkesselventricle with guiding balloon as a new approach for assisted circulation", Medical Instrumentation, vol. 10, No. 5, Sep.-Oct. 1976.

W.C. Birtwell, et al., "The evoloution of counterpulsation techniques", Medical Instrumentation, vol. 10, No. 5, Sep.-Oct. 1976.

* cited by examiner

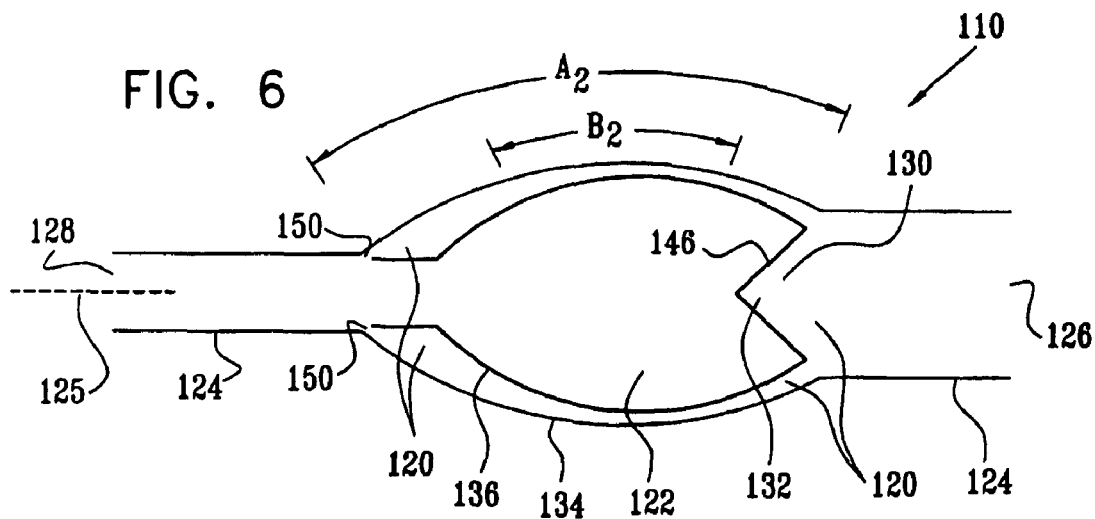
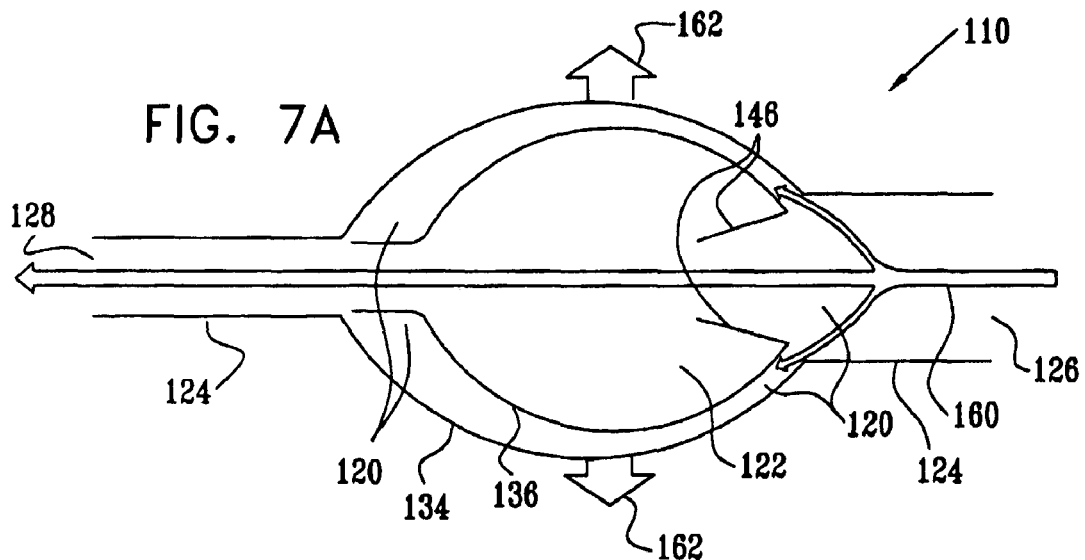
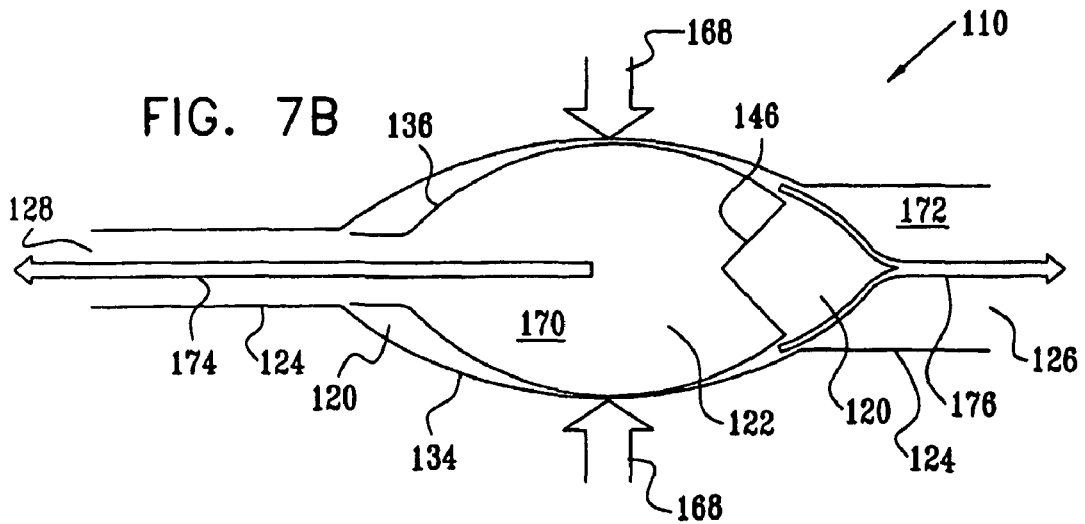

EXTRACARDIAC BLOOD FLOW AMPLIFICATION DEVICE

CROSS-REFERENCES TO RELATED APPLICATIONS

This application claims priority from U.S. Provisional Patent Application 60/543,700, filed Feb. 10, 2004, entitled, "Extracardiac blood flow amplification device," which is assigned to the assignee of the present application and is incorporated herein by reference.

FIELD OF THE INVENTION

The present invention relates generally to implantable medical devices, and specifically to methods and apparatus for implantable devices for treating conditions caused by insufficient blood circulation.

BACKGROUND OF THE INVENTION

Numerous medical conditions are caused by insufficient blood flow to certain tissues. For example, angina and myocardial infarction are caused by insufficient blood flow to cardiac muscle, and ischemic stroke is caused by insufficient blood flow to the brain. Renal failure or hypertension is caused by insufficient blood flow to the kidneys. Claudication results from poor circulation of blood in the leg arteries, typically caused by atherosclerosis as a result of smoking, diabetes, or high cholesterol. In some cases, particularly in diabetes, poor blood circulation in the leg results in amputation. Erectile dysfunction is sometimes caused by insufficient blood flow in the arteries supplying blood to the penis. Retinal vessel occlusion (retinal artery or vein occlusion) often results in vision loss.

Heart failure is a chronic cardiac condition characterized by a deficiency in the ability of the heart to pump blood. Decreased cardiac output to the systemic circulation typically increases venous blood pressure, which often leads to blood backing up in the lungs. Low cardiac output also results in decreased blood perfusion to organs, such as the liver, kidney, brain, and heart itself. Over time, the effects of heart failure contribute to a worsening of the condition. Reduced blood supply to the heart causes less effective contraction of the heart. At the same time, higher venous blood pressure increases the heart preload. To compensate, the heart attempts to increase output by increasing muscle strength, which leads to myocardial hypertrophy (enlargement of the heart with thickening and stiffening of the heart wall). These conditions in turn lead to reduced cardiac output, resulting in a vicious cycle.

There are primarily two types of heart failure, systolic heart failure and diastolic heart failure. Systolic heart failure is characterized by a deficiency in systolic heart function, which causes insufficient expulsion of blood during systole. Diastolic heart failure is characterized by a deficiency in diastolic heart function, which causes insufficient ventricular filling during diastole.

Counterpulsation is a technique for assisting the circulation by decreasing the afterload of the left ventricle and augmenting the diastolic pressure. Devices for achieving counterpulsation include intra-aortic balloons, pumping devices implantable in the chest, and external devices that apply a negative pressure to the lower extremities during cardiac systole. Counterpulsation devices are typically synchronized with a patient's cardiac cycle to apply pressure to blood vessels of the patient during diastole, and to remove the applied pressure immediately prior to systole, so as to increase stroke volume by decreasing afterload, to reduce heart workload, and to maintain or increase coronary perfusion.

Counterpulsation techniques have been studied since the mid-1950s. Birtwell WC et al., in "The evolution of counterpulsation techniques," Med. Instrum. 10:217-223 (1976), which is incorporated herein by reference, review the history of various counterpulsation techniques. Clauss RH et al., in "Assisted Circulation: 1. The Arterial Counterpulsator," Journal of Thoracic and Cardiovascular Surgery 41:447 (1961), which is incorporated herein by reference, describe a pump placed on the arterial side of the circulation and used to alter the pressure of the left intraventricular aortic and arterial pulses. Unger F et al., in "The Windkesselventricle with guiding balloon as a new approach to assisted circulation," Med. Instrum. 10:256-259 (1976), which is incorporated herein by reference, describe the implantation of balloons in aortas of dogs and a method for pneumatically driving the balloons synchronously with electrocardiogram (ECG) measurements, so as to increase hemodynamic efficiency.

Externally-applied counterpulsation devices are described, for example, in U.S. Pat. Nos. 5,554,103 and 5,997,540 to Zheng et al., and U.S. Pat. No. 3,866,604 to Curless et al., all of which are incorporated herein by reference. U.S. Pat. No. 5,514,079 to Dillon, which is incorporated herein by reference, describes techniques for improving circulation by applying external positive regional pressure on an extremity synchronously with the patient's heartbeat. An adjustable timing cycle is initiated at the QRS complex of the arterial pulse cycle. US Patent Application Publication 2002/0173735 to Lewis, which is incorporated herein by reference, describes a medical device for non-invasive counterpulsation treatment of heart disease and circulatory disorders through external cardiac assistance. The device comprises cuffs which are affixed on a patient's lower body and extremities, and which constrict by electromechanical activation, thereby augmenting blood pressure for treatment purposes.

PCT Publication WO 02/24254 to Khaghani et al., which is incorporated herein by reference, describes a blood circulation assistance device for location around a blood conduit. The device comprises an inflatable bladder for compressing the blood conduit to provide counterpulsation, and a pump for contracting and expanding the bladder. The pump expands the bladder at diastole, as determined by monitoring the cardiac cycle. An outer cuff surrounds the bladder in order to provide an outer limiting extent to the movement of the bladder.

U.S. Pat. No. 4,938,766 to Jarvik, which is incorporated herein by reference, describes implantable prosthetic devices and methods of use for increasing blood flow by increasing arterial compliance and reducing the magnitude of the pressure pulsations in the arterial system, and to increase perfusion of specific organs in order to overcome the deleterious effects of cardiovascular disease.

U.S. Pat. No. 6,030,336 to Franchi, which is incorporated herein by reference, describes a pump comprising variable volume means inserted in an artery, in particular, the descending aorta, enabling the volume through which the blood flows in this location to be modified cyclically and in a controlled manner. The device comprises a deformable enclosure in fluid communication with the variable volume. The variable volume and a spring coil urge the deformable enclosure against an increase of volume resulting from a pressure increase in the variable volume, and in the corresponding enclosure, so as to produce additional elastance for the artery during the heart cycle. In addition, an electric motor can control the deformable enclosure to increase or decrease its volume, and can exert its force in addition to or in subtraction from the force of the spring coil during the systolic and diastolic phases of the heart cycle.

U.S. Pat. No. 6,450,942 and European Patent Application 1 078 649 A1 to Lapanashvili et al., which are incorporated herein by reference, describe a technique for reducing heart load by measuring heart rhythm, and producing pressure pulsations in the peripheral vascular system in synchronization with the heart rhythm in a counterpulsation mode, so as to reduce pulse rate and/or systolic pressure, and thereby heart load.

U.S. Pat. Nos. 6,200,260, 6,299,575, and 6,428,464 to Bolling, and U.S. Pat. Nos. 6,387,037 and 6,390,969 to Boiling et al., all of which are incorporated herein by reference, describe an extracardiac pumping system comprising a pump implanted subcutaneously at a patient's groin. The pump draws blood from the patient's femoral artery and discharges blood to an artery that stems from the patient's aortic arch. The pump may be operated continuously or in a pulsatile fashion, synchronous with the patient's heart, thereby potentially reducing the pumping load on the heart.

U.S. Pat. No. 6,132,363 to Freed et al., which is incorporated herein by reference, describes a left ventricular-assist device comprising an inflatable bladder sutured into the wall of the descending thoracic aorta, a percutaneous access device (PAD) implanted in a hypogastric region of the patient and in fluid communication with the bladder, and a drive unit connectable through the PAD for selectively inflating and deflating the bladder.

US Patent Application Publication 2002/0151761 to Viole et al., which is incorporated herein by reference, describes an intravascular extracardiac system, comprising a pump with inflow and outflow conduits that are implanted intravascularly through a non-primary vessel, and positioned within the patient's vasculature. The pump is configured to be operated continuously or in a pulsatile fashion, synchronously with the patient's heart, thereby potentially reducing the afterload of the heart.

U.S. Pat. No. 3,585,983 to Kantrowitz et al. which is incorporated herein by reference, describes an intra-arterial cardiac-assist device having a balloon which is inflated periodically for diastolic augmentation. U.S. Pat. No. 4,630,597 to Kantrowitz et al., which is incorporated herein by reference, describes a dynamic aortic patch that is permanently surgically implanted in the wall of the aorta to augment the pumping action of the heart. The patch comprises an elongate semi-rigid shell member having a concave inner surface and a flexible membrane integrally bonded to the outer surface of the shell to define an inflatable and deflatable chamber between the concave inner surface and the membrane.

U.S. Pat. No. 4,240,409 to Robinson et al., which is incorporated herein by reference, describes a device for mechanically assisting circulation of blood in a patient for periods of up to two weeks until the patient's heart strengthens sufficiently to take over the full workload. The circulatory assist device includes a valveless pump with a flexible bladder, a pneumatic driver for applying pressure pulses to the bladder, and a single flexible conduit for conveying blood between the patient and the pump. In use, the pump and driver are mounted external to the patient's body and the flexible conduit is connected to the pump and in end-to-side relationship with a major blood vessel on that side of the heart, either right or left, which is in need of support.

U.S. Pat. No. 6,406,422 to Landesberg, which is incorporated herein by reference, describes a ventricular-assist system that utilizes an intraventricular device with a limited volume. The device is expanded at a critical time, for a critical duration, and with a volume change course such that it assists the pumping action of the heart without inducing stretching of the ventricular wall.

US Patent Application Publication 2002/0173693 to Landesberg, which is incorporated herein by reference, describes a system for assisting a failing ventricle, which utilizes a single blood displacement chamber and a single cannula. The cannula is inserted into the failing ventricle cavity and is connected to a blood displacement actuator. The device is described as producing blood displacement at a critical time for a critical duration and with blood flow time course such that it improves the systolic function of the heart, augments cardiac output, and increases the generated pressure. The device is also described as improving diastolic function by increasing the ventricle compliance and imposing rapid relaxation of the ventricle wall. The device is described as providing additional external work without deteriorating the mechanical function of the failing ventricle, moreover it is described as decreasing the energy consumption of the failing heart and improving coronary perfusion. Consequently, the device is described as improving the balance between the energy supply (coronary perfusion) to the ventricle wall and the mechanical demands, and to thereby allow recovery of the failing heart.

U.S. Pat. Nos. 6,673,043 and 6,511,413, also to Landesberg, describe related techniques to those described in the above-cited US Patent Application Publication 2002/0173693. These patents are incorporated herein by reference, as well.

U.S. Pat. No. 6,572,652 to Shaknovich, which is incorporated herein by reference, describes techniques for implanting a prosthetic valve in the pulmonary vein, in order to decrease or prevent an increase in pulmonary venous pressure. Expandable as well as fixed-dimension non-expandable pulmonary vein prosthetic valves for implantation by a variety of surgical and percutaneous procedures are described.

PCT Publication WO 98/57599 to Camilli, which is incorporated herein by reference, describes an implantable valve for use in blood vessels, particularly veins, more particularly venous confluences. The valve comprises a first supporting element in the shape of a bent body or of a cut sheet, and a second operative element in the shape of a leaflet, the two elements being joined one to another or the second one being integral with the first one. The valve is provided with anchor means and grip means to prevent longitudinal slipping when the valve is inserted in the blood vessel.

U.S. Pat. No. 6,299,637 to Shaolian et al., which is incorporated herein by reference, describes a self-expandable prosthetic venous valve, such as for implantation in the deep veins of the leg. The valve is mounted in a support structure, such as a self-expandable tubular wire cage.

US Patent Application Publication 2002/0103413 to Bugge et al., which is incorporated herein by reference, describes an implanted device for utilizing at least a part of the hydraulic energy generated by the heart to power various apparatus. The device typically includes a hydraulic motor powered by pressurized blood, which converts hydraulic energy into mechanical or electrical energy. The device typically stores the energy, and uses the stored energy to power an executing device, such as a pump or an electric motor. For some applications, the hydraulic motor is connected directly to one or more ventricles of the heart. Numerous embodiments of the device are described. For example, in one embodiment, the hydraulic motor is arranged as a unidirectionally acting pressure box in the form of two bellows connected in series, and with different cross-sectional areas resulting in the device's working as a differential piston. The bellows expand longitudinally against a return spring. Between the bellows is arranged a pusher plate having a valve that opens during diastole. A second valve is arranged at an opening of the smaller bellows for emptying the device. This valve opens during systole, at the same time as the return spring is compressed. In another embodiment, which is not described as having any valves, a counterpulsator includes the hydraulic motor and a pump, arranged as concentric bellows which are interconnected by a common pusher plate located within each other.

U.S. Pat. No. 4,527,549 to Gabbay, which is incorporated herein by reference, describes techniques for providing improved cardiac assist by the use of a intraaortic balloon. A single small balloon is placed in the ascending aorta close to the aortic valve, such placement being described as effective for producing a substantially stronger augmentation of heart action than with the use of a longer balloon normally placed, for example, in the descending aorta. Multiple small balloons positioned in the aortic arch, with or without a large balloon in the descending aorta, can be used to provide even stronger coronary flows.

U.S. Pat. No. 6,730,118 to Spenser et al., which is incorporated herein by reference, describes a valve prosthesis device suitable for implantation in body ducts. The device comprises a support stent, comprised of a deployable construction adapted to be initially crimped in a narrow configuration suitable for catheterization through the body duct to a target location and adapted to be deployed by exerting substantially radial forces from within by means of a deployment device to a deployed state in the target location, and a valve assembly comprising a flexible conduit having an inlet end and an outlet, made of pliant material attached to the support beams providing collapsible slack portions of the conduit at the outlet. The support stent is provided with a plurality of longitudinally rigid support beams of fixed length. When flow is allowed to pass through the valve prosthesis device from the inlet to the outlet, the valve assembly is kept in an open position, whereas a reverse flow is prevented as the collapsible slack portions of the valve assembly collapse inwardly providing blockage to the reverse flow.

SUMMARY OF THE INVENTION

In some embodiments of the present invention, an extracardiac fully-implantable blood flow amplification device is provided for placement in fluid communication with an artery of a subject. The device typically does not comprise a power supply for powering the device's blood flow amplification. The device comprises a first flexible chamber and a second flexible chamber in fluid communication with a first volume and a second volume of arterial blood, respectively. The first chamber and second chamber have a first surface and a second surface, respectively, both of which are in mechanical communication with a common surface that provides an elastically-derived force. The device further comprises a pressure-sensitive (unidirectional) valve coupled between the first chamber and the second chamber, the valve adapted to: (a) be in an open position during at least a portion of systole when a pressure gradient thereacross is greater than a threshold value, such that when the valve is in the open position, the first chamber is in fluid communication with the second chamber and the first volume is in fluid communication with the second volume, and (b) be in a substantially closed position during diastole when the pressure gradient is less than the threshold value, such that when the valve is in the closed position, the first chamber is substantially not in fluid communication with the second chamber and the first volume is substantially not in fluid communication with the second volume. Typically, an area of the first surface is greater than an area of the second surface.

During a systolic phase of operation of the implanted device, the valve opens and blood enters the first and second flexible chambers, expanding the chambers and applying systolic blood pressure to the first and second surfaces, respectively. The first and second surfaces apply force generated by the systolic blood pressure to the common surface, thereby storing potential energy in the source of the surface's elastically-derived force.

During a subsequent diastolic phase of operation, the valve closes, and the common surface converts the stored potential energy to kinetic energy, applying force to both the first and second surfaces. However, because during diastole the resistance against movement of the blood in the second chamber (the "pressurized blood") out of the second chamber is substantially greater than the resistance against movement of the blood in the first chamber (the "upstream blood") out of the first chamber, the common surface applies a disproportionately large portion of the stored potential energy to the second chamber. In this configuration, greater force is applied by the common surface to the second chamber during diastole than the second chamber applied to the common surface during systole. The force applied to the second chamber generates a pressure in the pressurized blood that is greater than diastolic blood pressure in the artery, and is typically greater than systolic blood pressure in the artery. The device thus provides increased blood circulation to tissue distal thereto, thereby treating conditions caused by insufficient blood circulation.

In some embodiments of the present invention, the first chamber comprises: (a) a first sub-chamber, in fluid communication with the first volume of arterial blood, and coupled to the valve; and (b) a second sub-chamber, having the first surface, such that the first sub-chamber and the second sub-chamber are shaped so as to define a first opening therebetween.

Alternatively or additionally, the second chamber comprises: (a) a primary sub-chamber, in fluid communication with the second volume of arterial blood, and coupled to the valve; and (b) a secondary sub-chamber, having the second surface, such that the primary sub-chamber and the secondary sub-chamber are shaped so as to define a second opening therebetween.

Typically, the second opening has an area less than an area of the first opening. For some applications, the first sub-chamber and the primary sub-chamber are arranged so as to form a lumen having a proximal end in fluid communication with the first volume of arterial blood, and a distal end in fluid communication with the second volume of arterial blood. Typically, the distal end has a diameter less than a diameter of the proximal end.

For some applications, the second sub-chamber and the secondary sub-chambers are positioned such that the second sub-chamber substantially surrounds the secondary sub-chamber. Alternatively, the second sub-chamber and the secondary sub-chamber are arranged side-by-side.

In some embodiments of the present invention, the source of the common surface's elastically-derived force comprises at least one spring. For some applications, the spring is positioned around the second sub-chamber and/or the first sub-chamber, typically in contact with the perimeter of the common surface. Alternatively, the spring is positioned in contact with a surface of the common surface opposite a surface of the common surface in contact with the first and second surfaces of the first and second chambers, respectively.

In some embodiments of the present invention, the common surface comprises a flexible, elastic material that provides the elasticity of the common surface. For some applications, the first surface comprises the common surface. Alternatively, the common surface comprises a hollow casing comprising an inner flexible wall in mechanical communication with the first and second surfaces. Pressure applied to the inner wall causes a gas within the hollow casing to compress, thereby storing potential energy and providing the elasticity of the common surface.

The implanted device is typically used to treat various medical conditions caused by insufficient blood circulation in a portion of the circulatory system. Conditions treatable by the device include, but are not limited to:

- conditions caused by poor blood circulation within a coronary artery, such as angina and myocardial infarction, typically caused by occlusion of the coronary artery. For treating such conditions, the device is coupled to a conventional coronary artery bypass graft providing blood flow from an aorta to the occluded coronary artery. Alternatively, the device is coupled to the ascending aorta of the subject, and a tube coupled to the second chamber of the device is passed through the wall of the aorta and coupled to the coronary artery, thereby providing sufficient blood circulation to the coronary artery;
- conditions caused by poor blood circulation in the legs, such as claudication, typically caused by atherosclerosis as a result of smoking, diabetes, or high cholesterol. For treating such conditions, the device is coupled to an artery in a leg of a subject, such as an iliac or a femoral artery, proximal to the atherosclerotic site;
- conditions caused by poor blood circulation to a kidney, such as renal failure and hypertension. For treating such conditions, the device is coupled to a renal artery supplying blood to the kidney;
- conditions caused by poor blood circulation to a portion of a brain, such as stroke. For treating such conditions, the device is typically coupled to an internal carotid artery;
- conditions caused by poor blood circulation to the eye, such as retinal vessel occlusion (retinal artery or vein occlusion). For treating such conditions, the device is typically coupled to an internal carotid artery or to an ophthalmic artery supplying blood to the eye;
- conditions caused by poor blood circulation to the penis, such as some forms of erectile dysfunction. For treating such conditions, the device is typically coupled to a penile artery or a dorsal penile artery, in order to provide increased blood flow to a corpus cavernosum and/or a corpus spongiosum of the penis, thereby enabling an erection; or
- conditions caused by poor blood flow from the lungs to the left atrium, such as diastolic heart failure. For treating such conditions, the device is typically coupled to a pulmonary vein.

In some embodiments of the present invention, an extracardiac fully-implantable blood flow amplification device is provided for placement in fluid communication with a blood vessel of a subject, such as a vein, e.g., a pulmonary vein. The device is configured to utilize the increased blood pressure during systole in a artery, e.g., a descending thoracic aorta, to increase blood flow through the blood vessel. When the blood vessel includes a pulmonary vein, the device typically treats diastolic heart failure by increasing the flow of blood from a lung to a left atrium of the subject. The device typically does not comprise a power supply for powering the device's blood flow amplification.

The device typically comprises a first flexible chamber, a second flexible chamber, and a base chamber in fluid communication with the first chamber. The device further comprises (a) inflow and outflow conduits, which are in fluid communication with the base chamber, and are adapted to be coupled to the blood vessel, and (b) a pressure conduit, in fluid communication with the second chamber, and adapted to be coupled to the artery, such that a pressure-transmitting fluid is in pressure communication with the blood of the artery.

The first chamber and the second chamber define a first surface and a second surface, respectively, each of which surfaces is in mechanical communication with a common surface that applies an elastically-derived force. The common surface is adapted to facilitate storage, as potential energy, of the work applied thereto by the first and second surfaces.

The device comprises a pressure-sensitive valve, positioned within the inflow conduit or between the inflow conduit and the base chamber. The valve is configured to bias blood flow in the direction from the first site to the base chamber. The valve is typically in an open position only when a pressure gradient thereacross is greater than a threshold value.

During a systolic phase of operation of the implanted device, the increased systolic pressure of the arterial blood is communicated to the pressure-transmitting fluid. This increased pressure is applied to the second surface, expanding the second chamber, and applying force to the common surface, thereby storing potential energy in the source of the elastically-derived force. Motion of the common surface expands the first chamber, opening the valve and drawing blood into the first chamber and the base chamber. During a subsequent diastolic phase of operation, the decreased diastolic pressure of the arterial blood is communicated to the pressure-transmitting fluid, resulting in lower pressure in the second chamber. The common surface converts the stored potential energy to kinetic energy, applying a force to both the first and second surfaces, thereby contracting the chambers. The valve closes, and the first chamber expels the blood downstream. The device thus increases blood flow through the blood vessel.

In some embodiments of the present invention, a diastolic heart failure treatment system comprises a blood flow regulation device. The device is adapted to be coupled in pressure communication with an artery of a subject, typically a descending thoracic aorta, and in fluid communication with a left atrium of the subject. The device is configured to utilize the increased blood pressure of aortic blood during systole to suck atrial blood from the left atrium into the device. The sucking of atrial blood from the left atrium lowers the blood pressure in the left atrium, thereby increasing blood flow from the pulmonary veins into the left atrium. This increased blood flow reduces backing up of blood in the lungs, and typically serves to treat diastolic heart failure.

The system typically further comprises one or more pressure-sensitive unidirectional valves. Each of the valves is implanted in one of the pulmonary veins of a subject. The valves are configured to substantially prevent backflow of blood from the pulmonary veins to the lungs. For some applications, the valves utilize techniques described in one or more of the above-mentioned U.S. Pat. No. 6,572,652 to Shaknovich, PCT Publication WO 98/57599 to Camilli, and U.S. Pat. No. 6,299,637 to Shaolian et al.

In some embodiments of the present invention, a blood flow amplification device is provided for placement in fluid communication with a vein and an artery of a subject. The device is configured to utilize the increased blood pressure in the artery during systole to increase blood flow in the vein. It is to be noted that the use of the device typically never brings arterial blood and venous blood into fluid communication with one another.

The device comprises a first flexible chamber, a second flexible chamber, an arterial conduit, and a venous conduit. The arterial conduit is coupled to and in fluid communication with the first chamber, and is adapted to be coupled to the artery. The venous conduit is coupled to and in fluid communication with the second chamber, and is adapted to coupled to the vein, typically by coupling a proximal inflow end of the conduit to a first site of the vein, and a distal outflow end of the conduit to a second site of the vein, the second site distal to the first site with respect to blood circulation.

The first chamber and the second chamber define a first surface and a second surface, respectively, each of which surfaces is in mechanical communication with a common surface that applies an elastically-derived force. The common surface is adapted to facilitate storage, as potential energy, of the work applied thereto by the first and second surfaces. The venous conduit further comprises a pressure-sensitive valve, which typically is in an open position only when a pressure gradient thereacross is greater than a threshold value.

During a systolic phase of operation of the device, arterial blood from the artery enters the first chamber. The blood applies systolic blood pressure to the first surface, thereby expanding the first chamber and applying force generated by the systolic blood pressure to the common surface, and storing potential energy in the source of the elastically-derived force. Also during systole, the valve opens and venous blood flows through the venous conduit because of the natural pressure of the venous blood. During a subsequent diastolic phase of operation, the common surface converts the stored potential energy to kinetic energy, applying a force to both the first and second surfaces, thereby contracting the chambers. The increased pressure in the second chamber and the venous conduit causes the valve to close. The resistance to movement of the venous blood distal to the valve is substantially greater than the resistance to movement of the diastolic arterial blood. In this configuration, during diastole, the common surface applies a disproportionately large portion of the stored potential energy to the second surface of the second chamber. The force applied to the second chamber generates a pressure in the distal venous blood that is greater than normal blood pressure in the vein. As a result, the device drives the distal venous blood out of the outflow end at high pressure. The device thus provides increased blood circulation in the vein, thereby treating conditions caused by insufficient blood circulation in the vein.

As described hereinabove, the implanted device typically does not comprise a power supply for powering the device's counterpulsation operation (although the device may comprise a power supply for powering adjustment mechanisms or sensors coupled thereto, for example as described hereinbelow with reference to FIGS. 4 and 5). As used in the present application, including the claims, a "power supply" excludes the heart.

It is to be understood that whereas embodiments of the present invention are described hereinabove with respect to controlling blood flow by use of a valve that opens and closes in response to pressure changes, the scope of the present invention includes the use of valve means having substantially no moving parts, but which bias flow in a predetermined direction by virtue of the shape of the valve means.

There is therefore provided, in accordance with an embodiment of the present invention, apparatus including:

a first chamber and a second chamber, adapted to be in fluid communication with a first volume and a second volume of oxygenated blood of a subject, respectively, the first chamber and the second chamber having a first surface and a second surface, respectively;

a third surface adapted to apply an elastically-derived force, at least a first portion of the third surface in mechanical communication with the first surface, and at least a second portion of the third surface in mechanical communication with the second surface during at least a portion of a cardiac cycle; and a pressure-sensitive valve coupled between the first chamber and the second chamber, the valve adapted to:
be in an open position during at least a portion of systole, such that the first chamber is in fluid communication with the second chamber and the first volume is in fluid communication with the second volume, and
be in a substantially closed position during diastole, such that the first chamber is substantially not in fluid communication with the second chamber and the first volume is substantially not in fluid communication with the second volume.

In an embodiment, the apparatus is adapted to expel, during diastole, oxygenated blood having a blood pressure greater than systolic blood pressure in a vicinity of the apparatus.

In an embodiment, the first chamber includes: a first sub-chamber, adapted to be in fluid communication with the first volume, and coupled to the valve; and a second sub-chamber, having the first surface, and the first sub-chamber and the second sub-chamber are shaped so as to define an opening therebetween. Alternatively or additionally, the second chamber includes: a first sub-chamber, adapted to be in fluid communication with the second volume, and coupled to the valve; and a second sub-chamber, having the second surface, and the first sub-chamber and the second sub-chamber are shaped so as to define an opening therebetween.

For some applications, the first surface and the second surface are adapted to apply respective forces to the third surface during systole, causing the third surface to store the forces as potential energy, and the third surface is adapted to apply, during diastole, more of the stored potential energy to the second surface than to the first surface.

For some applications, the apparatus includes at least one spring, configured to provide the elastically-derived force. Alternatively or additionally, for some applications, the third surface includes an elastic material, adapted to provide the elastically-derived force.

In an embodiment, the first surface includes the third surface. Alternatively, in an embodiment, the first surface and the second surface together include the third surface.

In an embodiment, the first chamber is shaped so as to define a first opening between the first chamber and the first volume of blood, the second chamber is shaped to as to define a second opening between the second chamber and the second volume of blood, and the second opening has a diameter less than a diameter of the first opening.

For some applications, the apparatus is adapted to be coupled to an artery in a leg of the subject, a renal artery of the subject, an internal carotid artery of the subject, an ophthalmic artery of the subject, a pulmonary vein of the subject, a penile artery of the subject, a dorsal penile artery of the subject, a coronary artery of the subject, or a coronary artery bypass graft providing blood flow from an aorta of the subject to a coronary artery of the subject. For some applications, the apparatus is adapted to be implanted in a blood vessel of the subject containing the first volume and the second volume of oxygenated blood.

For some applications, the apparatus includes a volume adjustment mechanism, adapted to adjust a maximum volume of blood that the first and second chambers are able to hold.

In an embodiment, the first chamber and the second chamber each include a flexible material, and the first chamber and the second chamber are arranged such that the first chamber surrounds the second chamber. For some applications, the first chamber and the second chamber are substantially radially symmetrical around a common longitudinal axis of the first chamber and the second chamber. For some applications, the first chamber is shaped so as to define one or more small openings between the first chamber and the second volume of oxygenated blood.

In an embodiment, the first surface has a first surface area, and the second surface has a second surface area less than the first surface area. For some applications, the second surface area is between about 60% and about 80% of the first surface area. Alternatively, for some applications, the second surface area is between about 30% and about 60% of the first surface area.

For some applications, the apparatus includes a pressure adjustment mechanism, adapted to adjust a maximum pressure of blood within the second chamber during diastole. For some applications, the pressure adjustment mechanism includes an adjustable valve, positioned between the second chamber and the first chamber.

In an embodiment, the apparatus includes a hollow casing, which includes: the third surface, which includes an inner flexible wall of the hollow casing, in mechanical communication with the first surface and the second surface; and a gas contained within the casing, such that compression of the gas provides the elastically-derived force. For some applications, the inner flexible wall includes a metallic membrane.

In an embodiment, the apparatus includes a tube, coupled to the second chamber, the first chamber is adapted to be coupled to a first artery of the subject containing the first volume of oxygenated blood, and the tube is adapted to be coupled to a second artery of the subject containing the second volume of oxygenated blood. For some applications, the first artery includes an ascending aorta of the subject, the second artery includes a coronary artery of the subject, the first chamber is adapted to be coupled to the ascending aorta, and the tube is adapted to be passed through a wall of the ascending aorta and to be coupled to the coronary artery. For some applications, the first chamber is adapted to be positioned immediately outside the first artery. For some applications, the first chamber is adapted to be coupled to the first artery such that a portion of the first volume of oxygenated blood flows around the first chamber. For some applications, the apparatus includes a stent, adapted to hold the first chamber in place within the first artery.

In an embodiment, the first chamber includes:
a first sub-chamber, adapted to be in fluid communication with the first volume, and coupled to the valve; and
a second sub-chamber, having the first surface, and the first sub-chamber and the second sub-chamber are shaped so as to define a first opening therebetween, and
the second chamber includes:
a primary sub-chamber, adapted to be in fluid communication with the second volume, and coupled to the valve; and
a secondary sub-chamber, having the second surface, and the primary sub-chamber and the secondary sub-chamber are shaped so as to define a second opening therebetween.

For some applications, the second opening has an area less than an area of the first opening. For some applications, the second sub-chamber and the secondary sub-chambers are positioned such that the second sub-chamber substantially surrounds the secondary sub-chamber. Alternatively, for some applications, the second sub-chamber and the secondary sub-chambers are positioned such that the second sub-chamber and the secondary sub-chamber are side-by-side. Further alternatively, for some applications, the first sub-chamber and the primary sub-chamber are arranged so as to form a lumen having a proximal end in fluid communication with the first volume of blood, and a distal end in fluid communication with the second volume of blood. For some applications, the distal end has a diameter less than a diameter of the proximal end.

There is also provided, in accordance with an embodiment of the present invention, apparatus for placement in fluid communication with at least one blood vessel of a subject carrying oxygenated blood, including:
a valve, adapted to be open during at least a portion of systole, and to be closed during diastole; and
a first chamber and a second chamber, in fluid communication with one another via the valve, and
the apparatus is adapted to expel, during diastole, blood having a blood pressure greater than systolic blood pressure in a vicinity of the apparatus, without using material power from a power supply for expelling.

In an embodiment, the apparatus includes a surface adapted to apply an elastically-derived force, the first chamber and the second chamber are adapted to apply respective forces to the surface during systole, causing the surface to store the forces as potential energy, and the surface is adapted to apply more of the stored potential energy to the second chamber than to the first chamber during diastole. For some applications, the apparatus includes at least one spring, configured to provide the elastically-derived force. Alternatively or additionally, for some applications, the surface includes an elastic material, adapted to provide the elastically-derived force.

There is further provided, in accordance with an embodiment of the present invention, apparatus including a first chamber and a second chamber, in fluid communication with one another, the second chamber adapted to be placed in fluid communication with a coronary artery of a subject, the apparatus adapted to expel into the coronary artery, during at least a portion of diastole, blood having a blood pressure greater than systolic blood pressure in a vicinity of the apparatus, without using material power from a power supply for expelling.

There is still further provided, in accordance with an embodiment of the present invention, apparatus including a first chamber and a second chamber, in fluid communication with one another, the second chamber adapted to be placed in fluid communication with a coronary artery of a subject, the apparatus adapted to expel into the coronary artery, during at least a portion of diastole, blood having an apparatus-induced blood pressure greater than an apparatus-absent diastolic blood pressure in the absence of the apparatus during the portion of diastole, without using material power from a power supply for expelling.

There is yet further provided, in accordance with an embodiment of the present invention, apparatus including a first chamber and a second chamber, in fluid communication with one another, the second chamber adapted to be placed in fluid communication with a pulmonary of a subject, the apparatus adapted to expel into the pulmonary vein, during at least a portion of diastole, blood having an apparatus-induced blood pressure greater than an apparatus-absent diastolic blood pressure in the absence of the apparatus during the portion of diastole, without using material power from a power supply for expelling.

There is also provided, in accordance with an embodiment of the present invention, apparatus for placement in fluid communication with a blood vessel of a subject carrying oxygenated blood, including a counterpulsation device, the device adapted to expel, during diastole, blood having a blood pressure greater than systolic blood pressure in a vicinity of the device, without using material power from a power supply for expelling.

There is yet additionally provided, in accordance with an embodiment of the present invention, apparatus including:

a generally circular device, adapted to be placed in a primary artery of a subject, the generally circular device including:
  a generally circular, substantially stiff inner ring;
  a toroid-shaped flexible bladder, coupled around the inner ring, and adapted to be in an expanded position during systole, and to be compressed by at least a portion of an inner wall of the primary artery during diastole; and
  a pressure-sensitive valve coupled to the bladder, adapted to be in an open position during at least a portion of systole and in a substantially closed position during diastole; and
a tube, having a first end and a second end, the first end coupled to the bladder, and the second end adapted to be coupled to a secondary artery of the subject.

For some applications, the primary artery includes an ascending aorta of the subject, the secondary artery includes a coronary artery of the subject, the generally circular device is adapted to be placed in the ascending aorta, and the second end of the tube is adapted to be coupled to the coronary artery.

There is still additionally provided, in accordance with an embodiment of the present invention, apparatus including:

a first chamber, having a first surface adapted to apply an elastically-derived force, the first chamber adapted to positioned immediately outside a primary artery of a subject containing oxygenated blood, such that the first chamber is in fluid communication with the primary artery;
a second chamber, having a second surface in mechanical communication with the first surface during at least a portion of a cardiac cycle;
a pressure-sensitive valve coupled between the first chamber and the second chamber, the valve adapted to be in an open position during at least a portion of systole, and to be in a substantially closed position during diastole;
a tube having a first end and a second end, the first end coupled to the second chamber, and the second end adapted to be positioned within the primary artery in a vicinity of a secondary artery that branches off of the primary artery.

For some applications, the primary artery includes an ascending aorta of the subject, the secondary artery includes a coronary artery of the subject, the first chamber is adapted to be positioned immediately outside the ascending aorta, and the second end of the tube is adapted to be positioned within the ascending aorta in the vicinity of the coronary artery.

For some applications, the second end of the tube includes a nozzle, adapted direct, towards the secondary artery, blood exiting the tube. For some applications, the apparatus includes an inlet, adapted to be implanted at a junction of the primary artery and the secondary artery, and configured to increase uptake of blood exiting the tube.

There is yet additionally provided, in accordance with an embodiment of the present invention, apparatus including:

a first chamber and a second chamber, the first chamber and the second chamber having a first surface and a second surface, respectively;
a third surface adapted to apply an elastically-derived force, at least a first portion of the third surface in mechanical communication with the first surface, and at least a second portion of the third surface in mechanical communication with the second surface during at least a portion of a cardiac cycle;
an inflow conduit and an outflow conduit, both coupled to and in fluid communication with the first chamber, the inflow conduit adapted to be coupled to a first site of a blood vessel of a subject, and the outflow conduit adapted to be coupled to a second site of the blood vessel, such that the first chamber is in fluid communication with the blood vessel;
a pressure conduit, coupled to and in fluid communication with the second chamber, the pressure conduit adapted to contain a pressure-transmitting fluid, and to be coupled to an artery of the subject, such that the pressure-transmitting fluid is in pressure communication with arterial blood of the artery; and
a pressure-sensitive valve coupled between the first site of the blood vessel and the first chamber, the valve adapted to be in an open position during at least a portion of systole, and to be in a substantially closed position during diastole.

In an embodiment, the pressure-transmitting fluid includes the arterial blood, and the pressure conduit is adapted to be coupled to the artery such that the pressure conduit is in fluid communication with the artery.

For some applications, the pressure conduit includes a pressure-transfer mechanism, and the pressure conduit is adapted to be coupled to the artery such that the pressure conduit is in pressure communication with the artery, and not in fluid communication with the artery.

For some applications, a first area of the first surface is greater than a second area of the second surface.

For some applications, the blood vessel includes a pulmonary vein of the subject, and the inflow and outflow conduits are adapted to be coupled to the pulmonary vein. For some applications, the artery includes a descending thoracic aorta of the subject, and the pressure conduit is adapted to be coupled to the descending thoracic aorta.

There is still additionally provided, in accordance with an embodiment of the present invention, apparatus including a regulation unit, adapted to be implanted in a pulmonary vein of a subject, and configured to utilize systolic blood pressure of an artery of the subject to suck atrial blood from a left atrium of the subject into the regulation unit during a portion of a cardiac cycle.

For some applications, the apparatus includes an atrial conduit, coupled to the regulation unit, and adapted to be coupled to the left atrium, such that the atrial blood is in fluid communication with the regulation unit via the atrial conduit.

For some applications, the apparatus includes a pressure-sensitive unidirectional valve, adapted to be implanted in the pulmonary vein, and configured to substantially prevent backflow of blood from the pulmonary vein to a lung of the subject.

For some applications, the artery includes a descending thoracic aorta of the subject, and the regulation unit is adapted to utilize the systolic blood pressure of the descending thoracic artery.

For some applications, the regulation unit is configured to suck the atrial blood from the left atrium to an extent that treats diastolic heart failure of the subject.

In an embodiment, the apparatus includes a pressure conduit, coupled to and in fluid communication with the regulation unit, the pressure conduit adapted to contain a pressure-transmitting fluid, and to be coupled to the artery, such that the pressure-transmitting fluid is in pressure communication with arterial blood of the artery. For some applications, the pressure-transmitting fluid includes the arterial blood, and the pressure conduit is adapted to be coupled to the artery such that the pressure conduit is in fluid communication with the artery. For some applications, the pressure conduit includes a pressure-transfer mechanism, and the pressure conduit is adapted to be coupled to the artery such that the pressure conduit is in pressure communication with the artery, and not in fluid communication with the artery.

In an embodiment, the regulation unit includes: a flexible inner chamber, in pressure communication with arterial blood of the artery; and a flexible outer chamber, surrounding the inner chamber, and adapted to apply an elastically-derived force, the outer chamber in fluid communication with the atrial blood. For some applications, the regulation unit includes one or more substantially rigid members, coupled to the inner chamber and positioned to contact an inner surface of the outer chamber.

There is yet additionally provided, in accordance with an embodiment of the present invention, apparatus including:

a first chamber and a second chamber, the first chamber and the second chamber having a first surface and a second surface, respectively;

a third surface adapted to apply an elastically-derived force, at least a first portion of the third surface in mechanical communication with the first surface, and at least a second portion of the third surface in mechanical communication with the second surface during at least a portion of a cardiac cycle;

an arterial conduit, coupled to and in fluid communication with the first chamber, and adapted to be coupled to an artery of a subject;

a venous conduit, coupled to and in fluid communication with the second chamber, and adapted to be coupled to and in fluid communication with a vein of the subject; and a pressure-sensitive valve, positioned in the venous conduit upstream from the second chamber, the valve adapted to be in an open position during at least a portion of systole, and to be in a substantially closed position during diastole.

There is also provided, in accordance with an embodiment of the present invention, apparatus including a blood flow amplification device, adapted to be placed in fluid communication with a vein and an artery of a subject, and configured to utilize systolic blood pressure of the artery to increase blood flow in the vein.

The present invention will be more fully understood from the following detailed description of embodiments thereof, taken together with the drawings, in which:

BRIEF DESCRIPTION OF THE DRAWINGS

FIG. 6 is a schematic cross-sectional view of another blood flow amplification device, in accordance with an embodiment of the present invention;

FIGS. 7A and 7B are schematic cross-sectional views of the device of FIG. 6 during systole and diastole, respectively, in accordance with an embodiment of the present invention;

DETAILED DESCRIPTION OF EMBODIMENTS

Figure 1A:
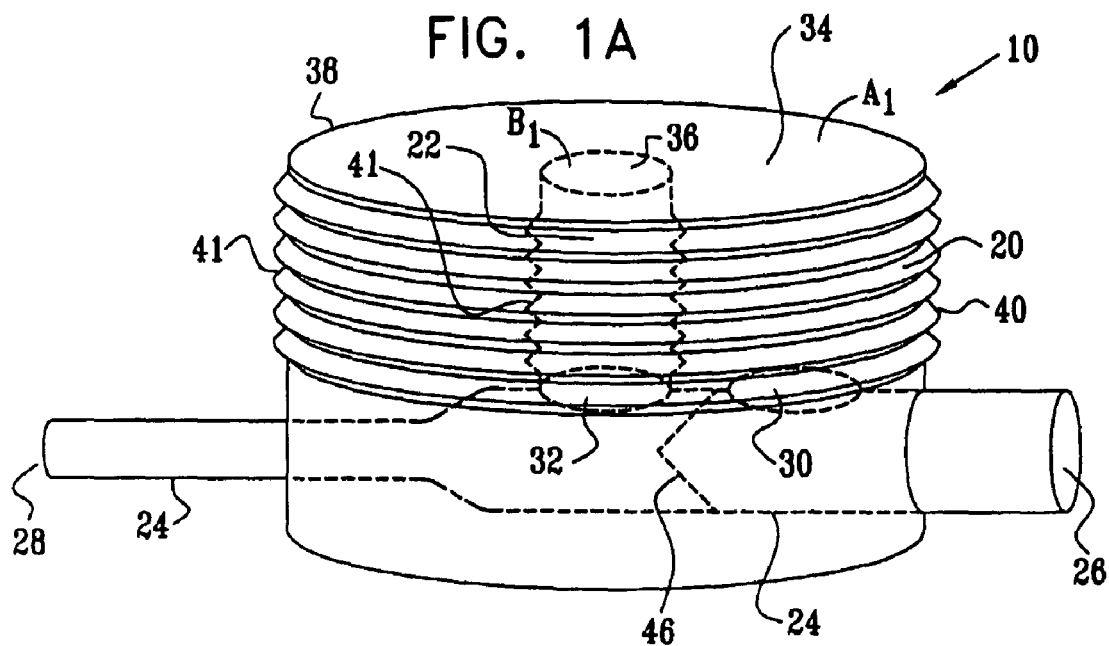
FIGS. 1A and 1B are a pictorial view and a schematic cross-sectional view, respectively, of a blood flow amplification device, in accordance with an embodiment of the present invention.
Figure 1B:
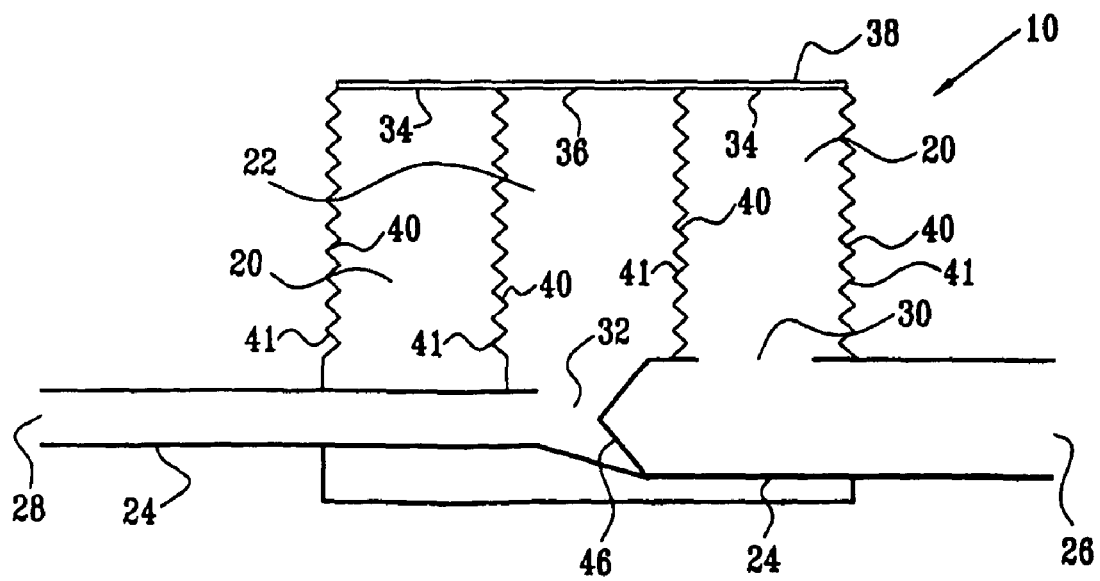

FIGS. 1A and 1B are a pictorial view and a schematic cross-sectional view, respectively, of an extracardiac fully-implantable blood flow amplification device 10, in accordance with an embodiment of the present invention. Device 10 comprises a first flexible chamber 20, a second flexible chamber 22, and a lumen 24. The lumen is adapted to be coupled to an artery (not shown) of a subject, by coupling a proximal inflow end 26 of the lumen to a first site of the artery, and a distal outflow end 28 of the lumen to a second site of the artery, the second site distal to the first site with respect to blood circulation. Typically, but not necessarily, a diameter of outflow end 28 is less than a diameter of inflow end 26. For example, the diameter of outflow end 28 may be between about 50% and about 80% of the diameter of inflow end 26.

In the embodiment shown in FIGS. 1A and 1B, the chambers are generally cylindrically shaped, and second chamber 22 is shown surrounded by first chamber 20. Alternatively, the chambers have different shapes, and/or first chamber 20 and second chamber 22 are arranged side-by-side, or in another arrangement (configurations not shown).

Lumen 24 is shaped so as to define a first opening 30 between the lumen and first chamber 20, and a second opening 32 between the lumen and second chamber 22. Typically, but not necessarily, second opening 32 has an area less than an area of first opening 30, such as between about 50% and about 80% of the area of first opening 30. For example, the area of first opening 30 may be between about 1 and about 2 cm$^2$, while the area of second opening 32 may be between about 0.5 and about 1 cm$^2$. First chamber 20 and second chamber 22 define a first surface 34 and a second surface 36, respectively, each of which surfaces is in mechanical communication with a common surface 38 that applies an elastically-derived force. For some applications, first surface 34 and second surface 36 together comprise surface 38.

Typically, first surface 34 has a surface area $A_1$, and second surface 36 has a surface area $B_1$, which is less than $A_1$. For example, $B_1$ may be between about 60% and about 80% of $A_1$, or, for some applications, between about 30% and about 60% of $A_1$. Depending upon the specific therapeutic application, $A_1$ is typically between about 5 and about 10 cm$^2$, and $B_1$ is typically between about 2.5 and about 5 cm$^2$. Also depending upon the specific therapeutic application, the volume of first chamber 20 is typically between about 10 and about 20 ml, and the volume of second chamber 22 is typically between about 5 and about 10 ml. For some applications, the volume of second chamber 22 is between about 25% and about 80% of the volume of first chamber 20.

Surface 38 is adapted to facilitate storage, as potential energy, of the work applied thereto by first surface 34 and second surface 36. For example, surface 38 may be generally rigid, and the source of the elastically-derived force applied to surface 38 may comprise one or more springs 40 integrated into walls 41 of first chamber 20 and second chamber 22, or into wall 41 of just one of the chambers (e.g., wall 41 of the second chamber 22). For some applications, discrete springs 40 are not provided, but instead the walls of one or both chambers are constructed so as to have inherent elastic properties. Alternatively, the source of the elastically-derived force applied to surface 38 comprises an external spring that surrounds the chambers and is fixed to surface 38 and/or the walls of the chambers (configuration not shown). Alternatively or additionally, at least a portion of the source of the elastically-derived force applied to surface 38 comprises two or more attracting magnets, for example as described in the above-mentioned U.S. Pat. No. 4,938,766 to Jarvik (configuration not shown). Other configurations for providing an elastically-derived force to surface 38 will be evident to those skilled in the art, having read the present application, and are included within the scope of the present invention.

Figure 2:
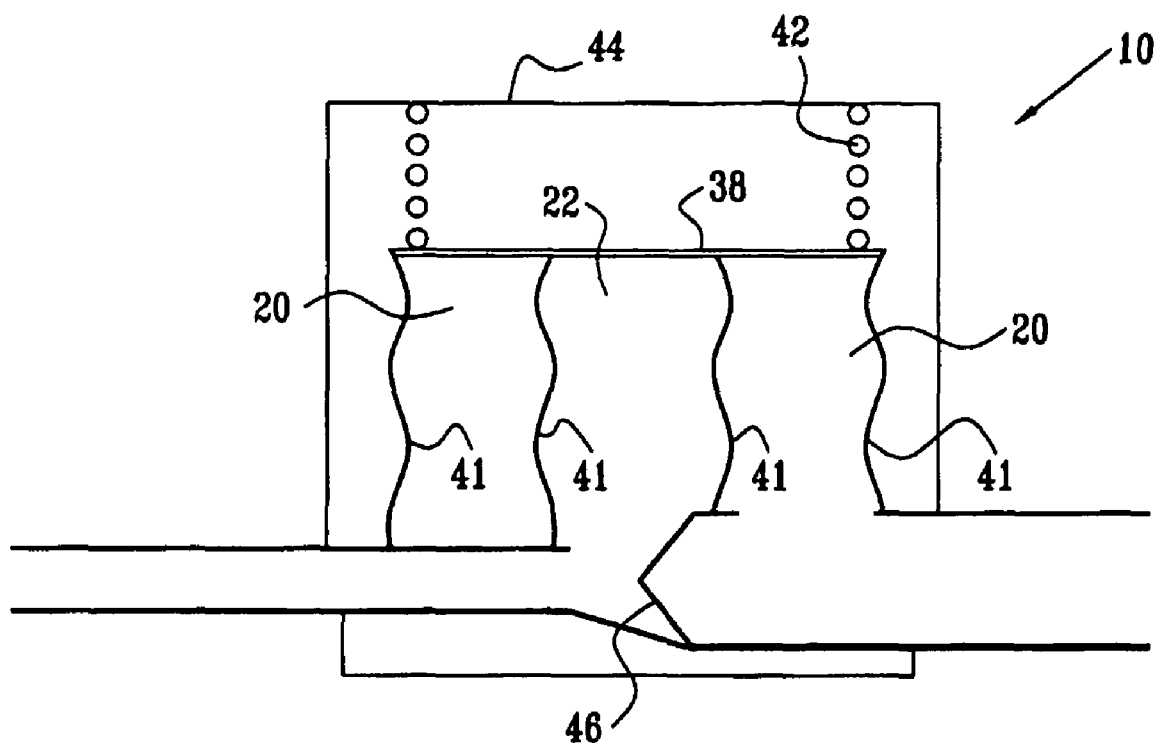
FIG. 2 is a schematic cross-sectional view of the device of FIGS. 1A and 1B, in accordance with an embodiment of the present invention.

FIG. 2 is a schematic cross-sectional view of device 10, in accordance with an embodiment of the present invention. In this configuration, the elastically-derived force is provided to surface 38 by at least one spring 42 positioned between surface 38 and an external casing 44 of device 10. Walls 41 of chambers 20 and 22 are typically, but not necessarily, flexible but non-elastic in this configuration.

Reference is again made to FIGS. 1A and 1B. Lumen 24 comprises a pressure-sensitive valve 46, positioned within the lumen such that: (a) during at least a portion of systole, valve 46 opens and blood throughout the lumen is in fluid communication with both first chamber 20 and second chamber 22, and (b) during diastole, valve 46 closes and blood proximal to valve 46 (i.e., in the direction of inflow end 26) is in fluid communication with first chamber 20 but substantially not second chamber 22, and blood distal to valve 46 is in fluid communication with second chamber 22 but substantially not first chamber 20. Valve 46 is typically in an open position only when a pressure gradient thereacross is greater than a threshold value, e.g., greater than between about 1 and about 4 mm Hg.

Figure 3A:
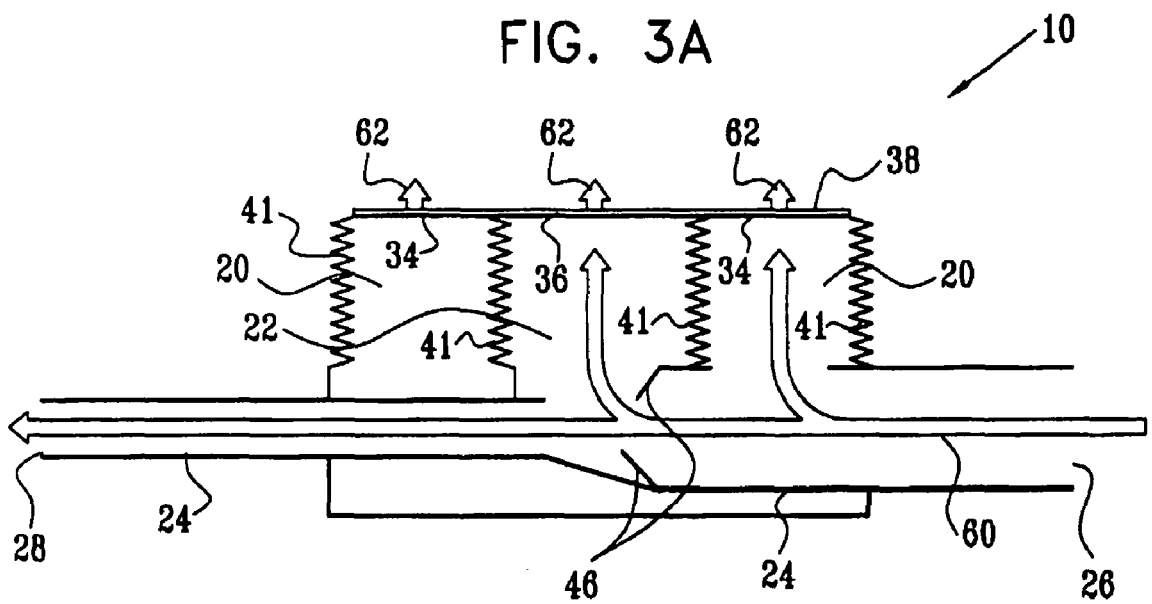
FIGS. 3A and 3B are schematic cross-sectional views of the device of FIGS. 1A and 1B during systole and diastole, respectively, in accordance with an embodiment of the present invention.
Figure 3B:
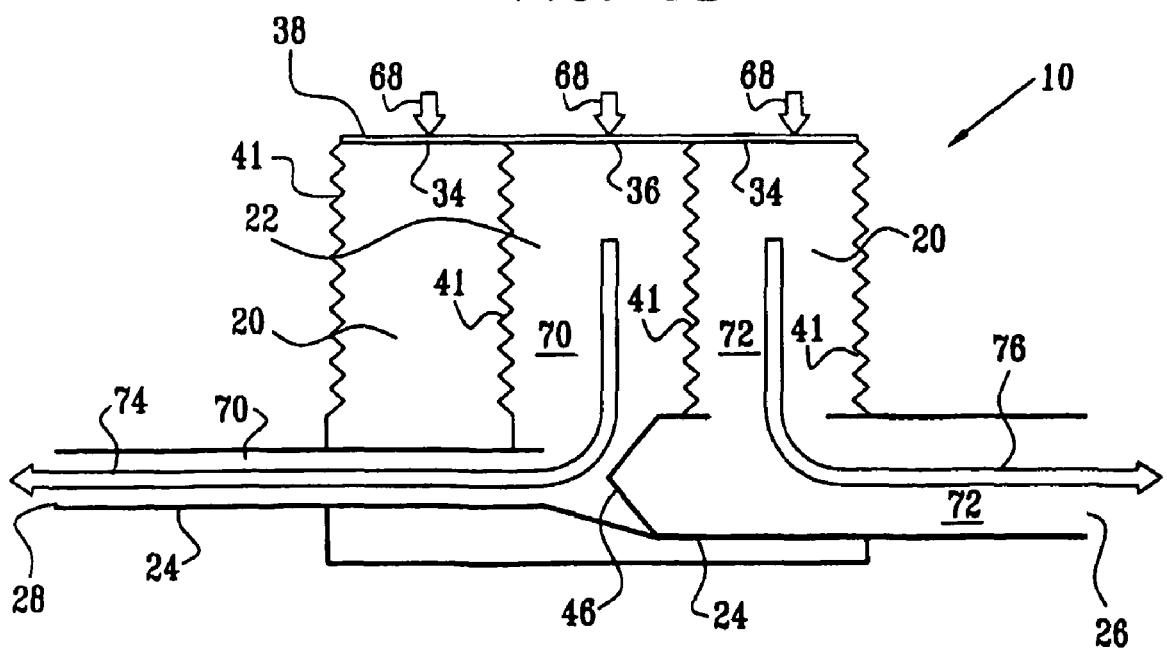

FIGS. 3A and 3B are schematic cross-sectional views of device 10 during systole and diastole, respectively, in accordance with an embodiment of the present invention. During a systolic phase of operation of device 10, as shown in FIG. 3A, valve 46 opens and blood, the flow of which is symbolically represented by an arrow 60, enters first chamber 20 and second chamber 22. The blood expands first chamber 20 and second chamber 22 in the direction indicated by arrows 62, applying systolic blood pressure to first surface 34 and second surface 36, respectively. The first and second surfaces apply force generated by the systolic blood pressure to surface 38, thereby storing potential energy in the source of the elastically-derived force. As described above, the source of the elastically-derived force may comprise the walls 41 of first chamber 20 and/or second chamber 22, or a spring 42 external to the chambers. As indicated by arrow 60, some of the blood also exits device 10 through outflow end 28.

During a subsequent diastolic phase of operation, as shown in FIG. 3B, valve 46 closes, and surface 38 converts the stored potential energy to kinetic energy, applying a force to both first surface 34 and second surface 36, thereby contracting the chambers in the direction indicated by arrows 68. For the purposes of the description hereinbelow, two volumes of blood are described: (a) "pressurized" blood 70, comprising the blood in second chamber 22 and the portion of lumen 24 distal to valve 46, and (b) "upstream" blood 72, comprising the blood in first chamber 20 and the portion of lumen 24 proximal to valve 46. During diastole, the resistance to movement of pressurized blood 70 from device 10 is substantially greater than the resistance to movement of upstream blood 72 from device 10. In this configuration, during diastole, surface 38 applies a disproportionately large portion of the stored potential energy to second surface 36 of second chamber 22. Correspondingly, greater force is applied by surface 38 to second chamber 22 during diastole than second chamber 22 applied to surface 38 during systole. The force applied to second chamber 22 generates a pressure in pressurized blood 70 that is greater than diastolic blood pressure in the artery, and is typically greater than systolic blood pressure in the artery. As a result, device 10 drives pressurized blood 70 out of outflow end 28 at high pressure, as indicated symbolically by arrow 74, and also drives upstream blood 72 out of inflow end 26 at lower pressure, as indicated symbolically by arrow 76. Device 10 thus provides increased blood circulation to tissue distal thereto, thereby treating conditions caused by insufficient blood circulation, such as those described hereinbelow with reference to FIGS. 8A-8F.

It is hypothesized that, for some applications, and under certain operating conditions, the relationship between the pressure of pressurized blood 70 and the pressure of upstream blood 72 may be approximated by the following equation:

$$P_p = P_u (A_1 / B_1)$$

wherein $P_p$ is the pressure of pressurized blood 70, $P_u$ is the pressure of upstream blood 72, $A_1$ is the surface area of first surface 34, and $B_1$ is the surface area of second surface 36 (as shown in FIG. 1A).

Figure 4:
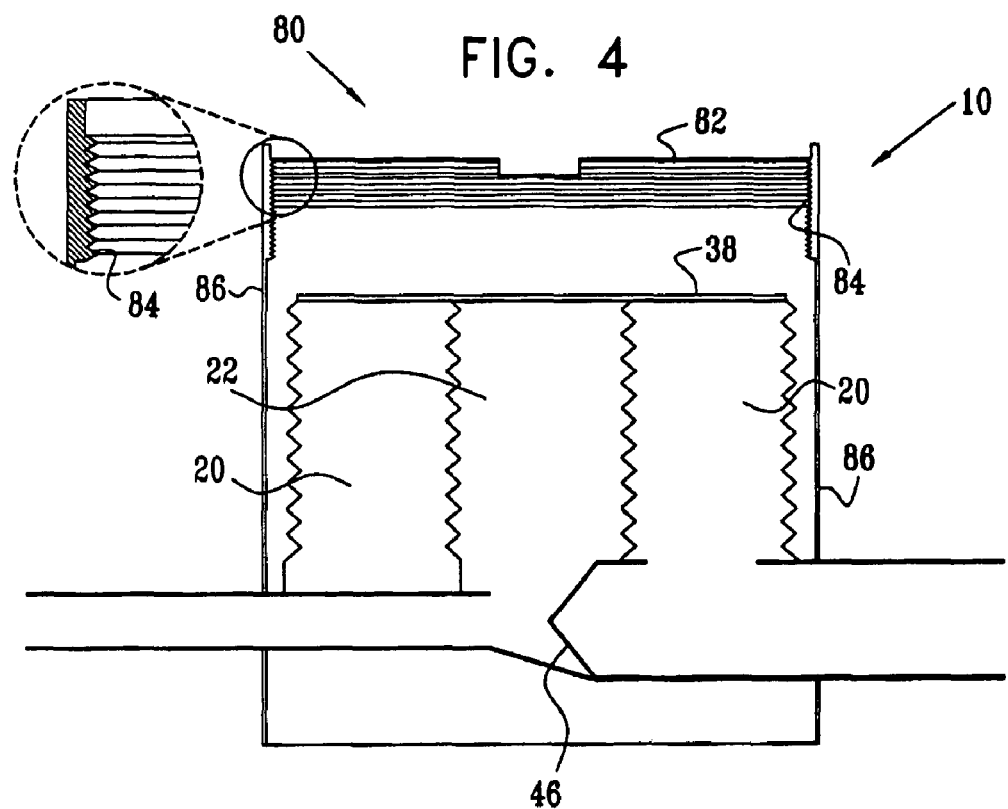
FIG. 4 is a schematic cross-sectional view of a volume adjustment mechanism of the device of FIGS. 1A and 1B, in accordance with an embodiment of the present invention.

FIG. 4 is a schematic cross-sectional view of a volume adjustment mechanism 80 of device 10, in accordance with an embodiment of the present invention. Mechanism 80 enables adjustment of the maximum volume of blood that chambers 20 and 22 are able to hold. In the embodiment shown in the figure, mechanism 80 comprises a screw 82, which screws into threads 84 defined by an inner surface of a casing 86 of device 10. As screw 82 is tightened, it increasingly constrains the maximum expansion of surface 38, and thus the maximum volume of chambers 20 and 22. Optionally, a motor adjusts screw 82, such as responsively to a physiological parameter measured by a sensor, e.g., a blood pressure sensor, and/or responsively to a timer or an external input (configuration not shown). Additional techniques for constraining the expansion of surface 38 will be evident to those skilled in the art, having read the present application, and are within the scope of the present invention.

Figure 5:
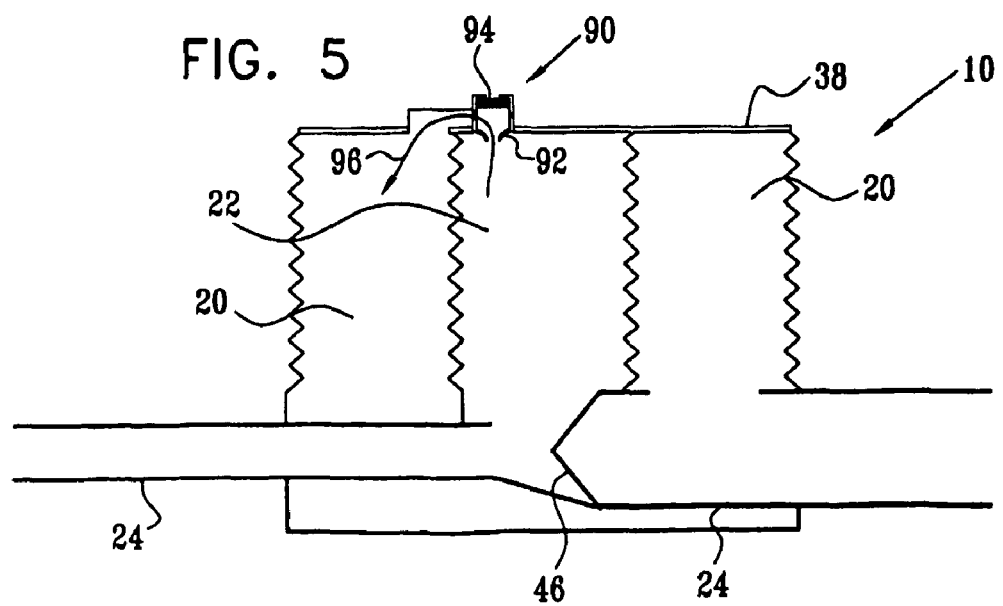
FIG. 5 is a schematic cross-sectional view of a pressure adjustment mechanism of the device of FIGS. 1A and 1B, in accordance with an embodiment of the present invention.

FIG. 5 is a schematic cross-sectional view of a pressure adjustment mechanism 90 of device 10, in accordance with an embodiment of the present invention. Mechanism 90 enables adjustment of the maximum pressure of blood within chamber 22 during diastole. In the embodiment shown in the figure, mechanism 90 comprises an adjustable valve 92, which is adjusted by a set screw 94. Opening of valve 92 allows a small amount of blood to pass from second chamber 22 to first chamber 20, as indicated by an arrow 96. Such passage lowers the pressure in second chamber 22 during diastole. Despite such passage, first chamber 20 remains substantially not in fluid communication with second chamber 22 when valve 46 is closed. Optionally, a motor adjusts set screw 94, such as responsively to a physiological parameter measured by a sensor, e.g., a blood pressure sensor, and/or responsively to a timer or an external input (configuration not shown). Additional techniques for allowing variable passage of blood from second chamber 22 to first chamber 20 (e.g., conventional pressure regulation techniques, or the use of a relief valve) will be evident to those skilled in the art, having read the present application, and are within the scope of the present invention.

FIG. 6 is a schematic cross-sectional view of an extracardiac fully-implantable blood flow amplification device 110, in accordance with an embodiment of the present invention. Device 110 comprises a first flexible chamber 120, a second flexible chamber 122, and a lumen 124. First flexible chamber 120 typically surrounds second flexible chamber 122, and both chambers are typically, but not necessarily, substantially radially symmetrical around a longitudinal axis 125 of lumen 124. Lumen 124 is adapted to be coupled to an artery (not shown) of a subject, by coupling a proximal inflow end 126 of the lumen to a first site of the artery, and a distal outflow end 128 of the lumen to a second site of the artery, the second site distal to the first site with respect to blood circulation. Typically, but not necessarily, a diameter of outflow end 128 is less than a diameter of inflow end 126. For example, the diameter of outflow end 128 may be between about 50% and about 80% of the diameter of inflow end 126.

Lumen 124 is shaped so as to define a first opening 130 between the lumen and first chamber 120, and a second opening 132 between the lumen and second chamber 122. First chamber 120 defines an elastic first surface 134, and second chamber 122 defines a second surface 136, which is flexible but not necessarily elastic. Alternatively, first surface 134 is not necessarily elastic, and a spring (e.g., a band) external to first surface 134 is positioned to provide elasticity to the surface (configuration not shown).

Typically, first surface 134 has a surface area $A_2$, and second surface 136 has a characteristic surface area $B_2$, which is less than about 50% of $A_2$. Surface area $B_2$ is defined as the surface area of the portion of inner chamber 122 that comes in contact with second surface 136 during diastole, as described hereinbelow with reference to FIG. 7B. For example, $B_2$ may be between about 30% and about 40% of $A_2$, or, for some applications, between about 10% and about 30% of $A_2$. Depending upon the specific therapeutic application, $A_2$ is typically between about 5 and about 15 cm$^2$, and $B_2$ is typically between about 2.5 and about 7.5 cm$^2$. Also depending upon the specific therapeutic application, the volume of first chamber 120 is typically between about 10 and about 20 ml, and the volume of second chamber 122 is typically between about 5 and about 10 ml.

Lumen 124 comprises a pressure-sensitive valve 146, positioned at second opening 132, such that: (a) during at least a portion of systole, valve 146 opens and blood in the lumen is in fluid communication with both first chamber 120 and second chamber 122, and (b) during diastole, valve 146 closes and blood proximal to valve 146 (i.e., in the direction of inflow end 126) is in fluid communication with first chamber 120 but substantially not second chamber 122, and blood distal to valve 146 is in fluid communication with second chamber 122 but substantially not with first chamber 120. Valve 146 is typically in an open position only when a pressure gradient thereacross is greater than a threshold value, e.g., greater than between about 1 and about 4 mm Hg.

For some applications, lumen 124 or first chamber 120 is shaped so as to define one or more small openings 150 between first chamber 120 and the portion of lumen 124 distal to second chamber 122. For example, openings 150 may be positioned radially around axis 125. Openings 150 may serve to allow a small portion of blood in first chamber 120 to flow through to the distal portion of lumen 124, thereby increasing the motion of the blood in first chamber 120 and reducing the likelihood of any potential coagulation of the blood. Despite this small flow, first chamber 120 remains substantially not in fluid communication with the distal portion of lumen 124 when valve 146 is closed. Typically, the aggregate volume of blood flow through openings 150 is less than about 10% of the total volume of blood flow through device 110, such as less than about 3% of the total blood flow through the device.

FIGS. 7A and 7B are schematic cross-sectional views of device 110 during systole and diastole, respectively, in accordance with an embodiment of the present invention. During a systolic phase of operation of device 110, as shown in FIG. 7A, valve 146 opens and blood, the flow of which is symbolically represented by an arrow 160, enters first chamber 120 and second chamber 122. The blood expands first chamber 120 and second chamber 122 in the direction indicated by arrows 162, applying systolic blood pressure to first surface 134 and second surface 136, respectively. Elastic first surface 134 expands, thereby storing potential energy therein.

During a subsequent diastolic phase of operation, as shown in FIG. 7B, valve 146 closes, and elastic first surface 134 applies the stored potential energy to both first chamber 120 and second chamber 122, contracting the chambers in the direction indicated by arrows 168. For the purposes of the description hereinbelow, two volumes of blood are described: (a) "pressurized" blood 170, comprising the blood in second chamber 122 and the portion of lumen 124 distal to valve 146, and (b) "upstream" blood 172, comprising the blood in first chamber 120 and the portion of lumen 124 proximal to valve 146. During diastole, the resistance to movement of pressurized blood 170 from device 110 is substantially greater than the resistance of upstream blood 172 from device 110. In this configuration, during diastole, elastic first surface 134 applies a disproportionately large portion of the stored potential energy to second chamber 122. Correspondingly, the force applied to second chamber 122 generates a pressure in pressurized blood 170 that is greater than diastolic blood pressure in the artery, and is typically greater than systolic blood pressure in the artery. As a result, device 110 drives pressurized blood 170 out of outflow end 128 at high pressure, as indicated symbolically by arrow 174, and also drives upstream blood 172 out of inflow end 126 at lower pressure, as indicated symbolically by arrow 176. Device 110 thus provides increased blood circulation to tissue distal thereto, thereby treating conditions caused by insufficient blood circulation, such as those described hereinbelow with reference to FIGS. 8A-8F.

For some applications, device 110 comprises a volume adjustment mechanism similar to mechanism 80 described hereinabove with reference to FIG. 4 (configuration not shown), mutatis mutandis. Alternatively or additionally, for some applications device 110 comprises a pressure adjustment mechanism, similar to mechanism 90 described hereinabove with reference to FIG. 5 (configuration not shown), mutatis mutandis.

FIGS. 8A-8F are schematic pictorial illustrations of the use of an extracardiac fully-implantable blood flow amplification device 200, such as device 10 or device 110, to treat various medical conditions, in accordance with embodiments of the present invention.

Figure 8A:
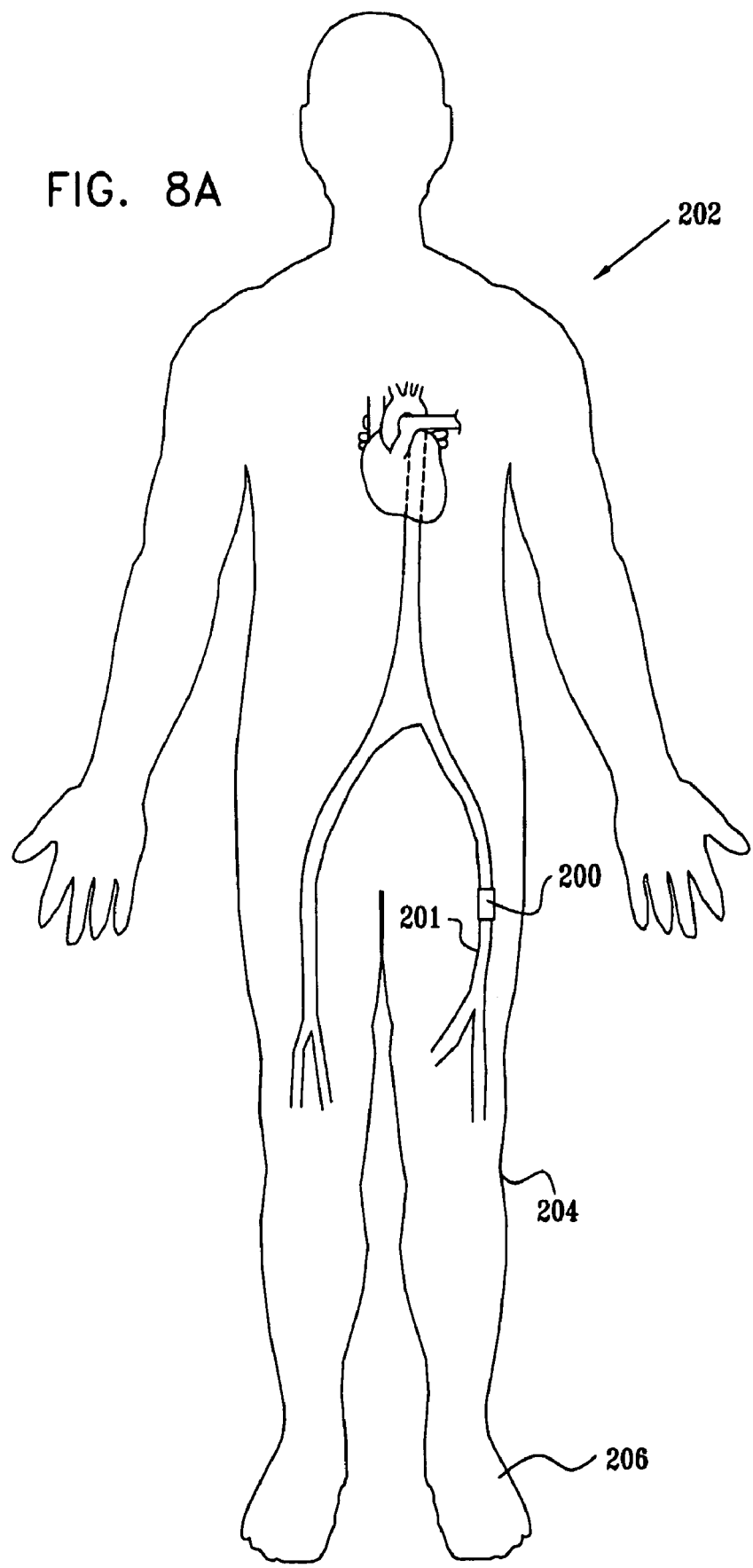
FIGS. 8A-8F are schematic pictorial illustrations of the use of a blood flow amplification device to treat various medical conditions, in accordance with embodiments of the present invention.

FIG. 8A shows device 200 coupled to an iliac artery 201 of a subject 202. Alternatively or additionally, device 200 is coupled to another artery in a leg 204 or a foot 206 of subject 202, such as a femoral artery. When deployed at one or more of these locations, device 200 provides increased blood flow and/or pressure to the leg arteries distal to the device, and therefore treats conditions caused by poor blood circulation in the leg arteries. Such conditions include, for example, claudication, typically caused by atherosclerosis as a result of smoking, diabetes, or high cholesterol.

Figure 8B:
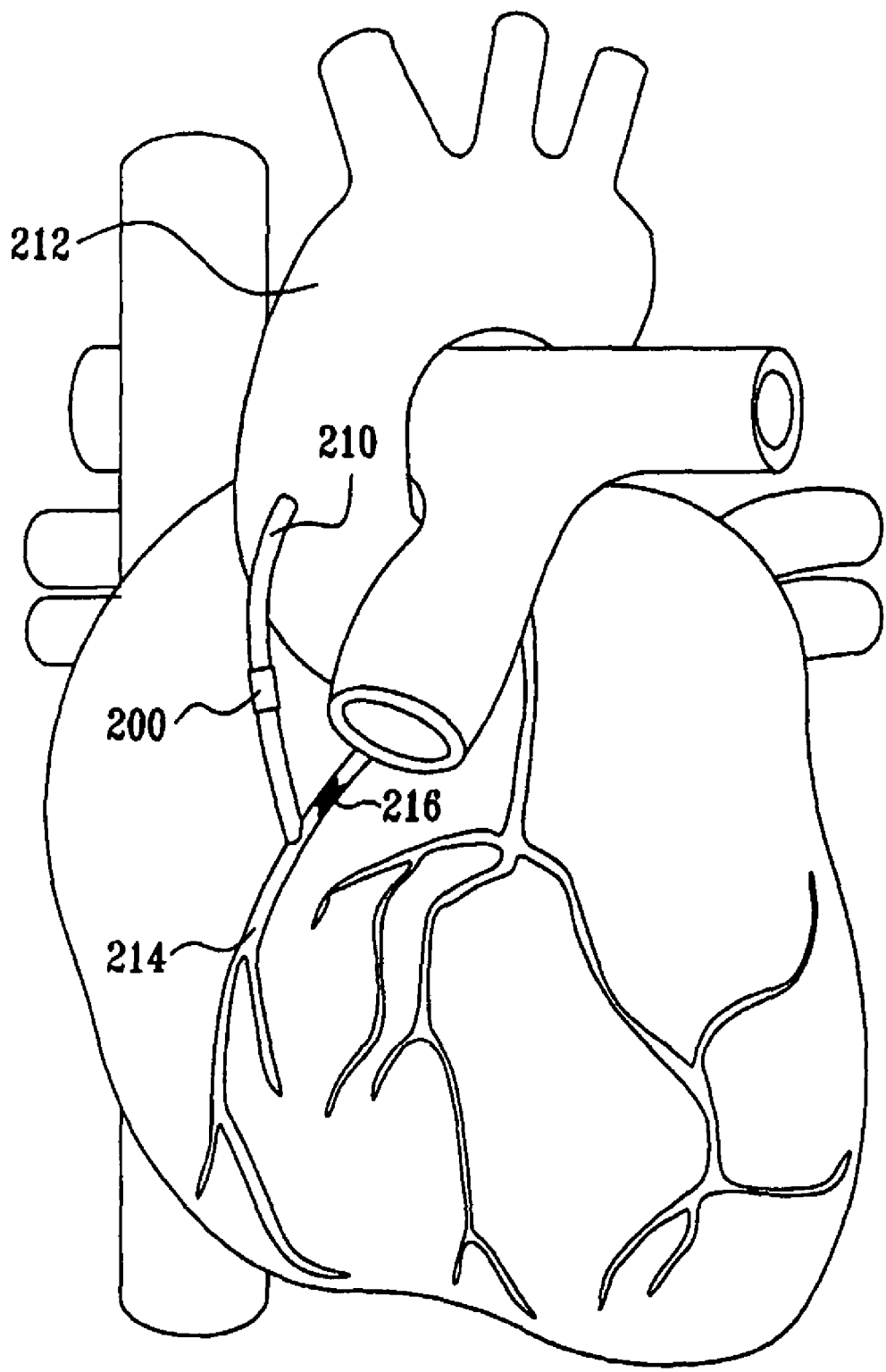

FIG. 8B shows device 200 coupled to a conventional coronary artery bypass graft 210 providing blood flow from an aorta 212 to a coronary artery 214 having a blockage 216. When deployed at this location, device 200 provides increased blood flow and/or pressure to coronary artery 214, and typically reestablishes sufficient blood flow in the occluded artery, treating conditions such as angina and myocardial infarction.

Figure 8C:
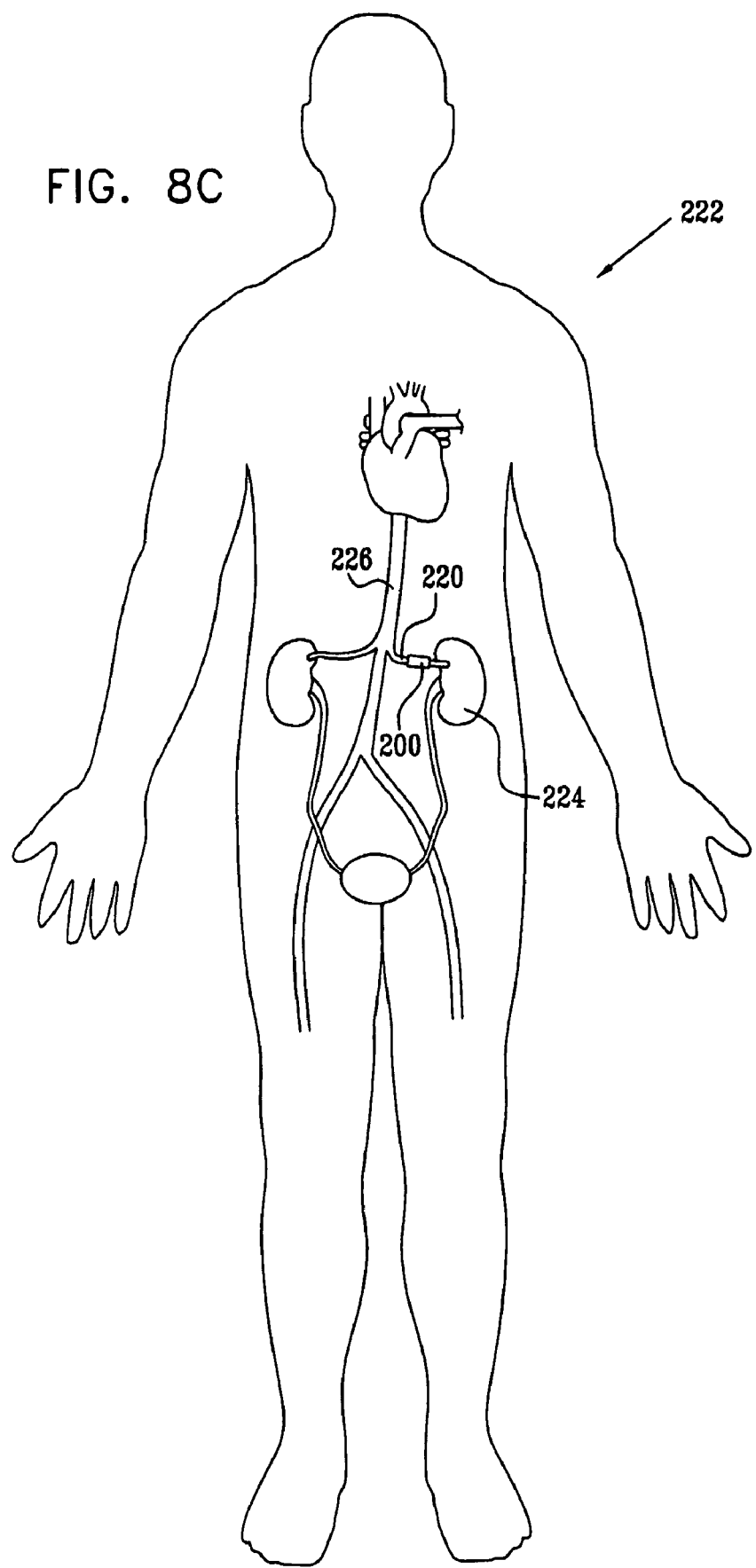
Figure 9A:
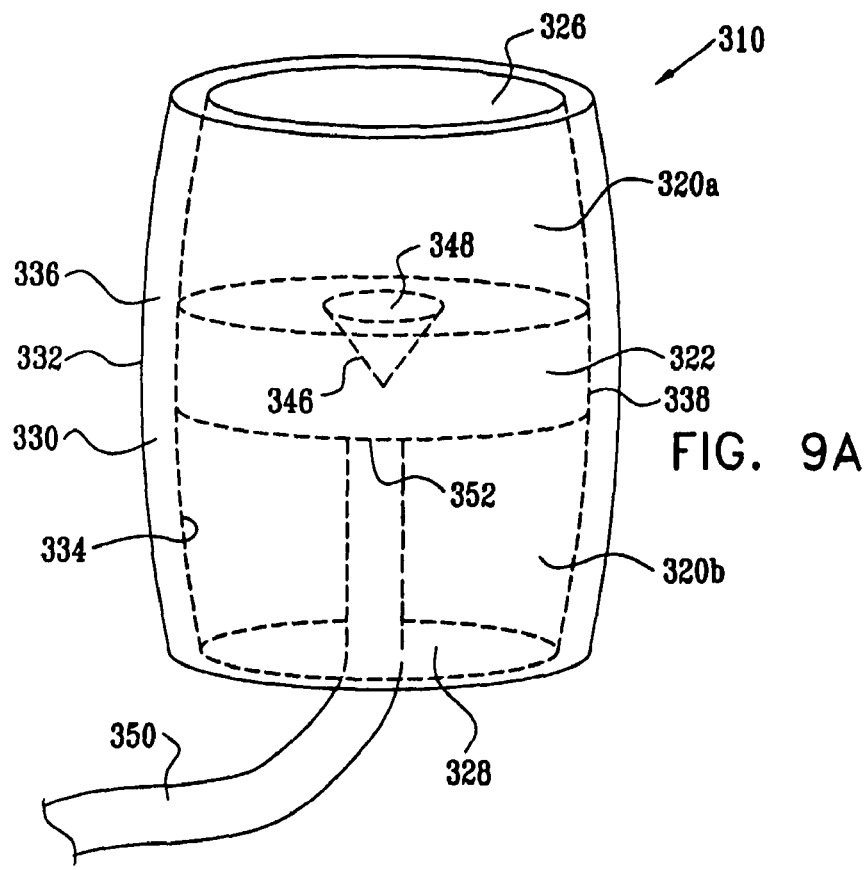
FIGS. 9A and 9B are a pictorial view and a schematic cross-sectional view, respectively, of yet another blood flow amplification device, in accordance with an embodiment of the present invention.
Figure 9B:
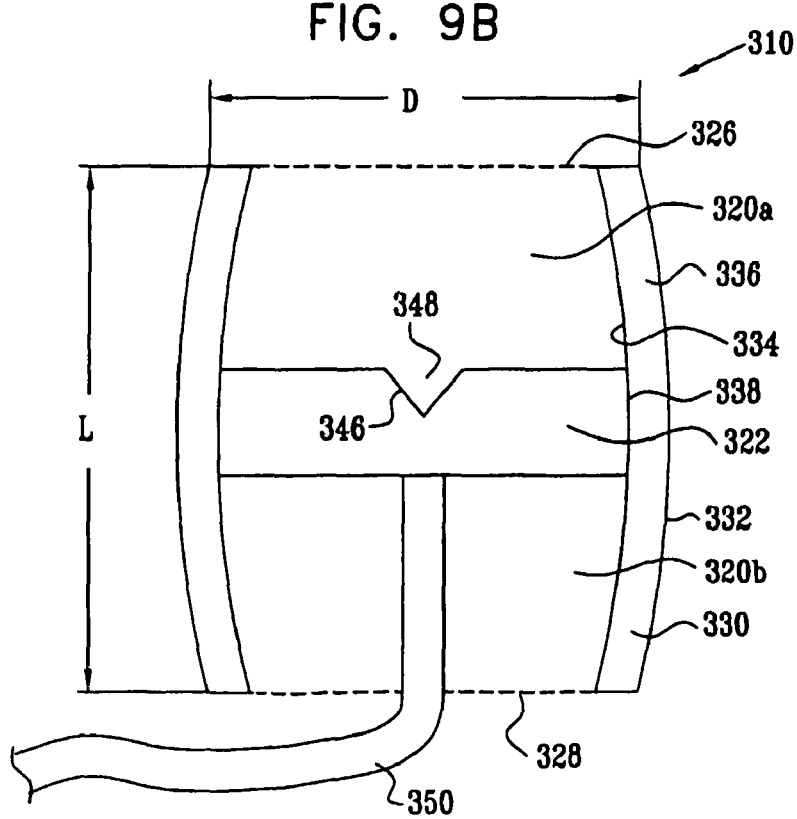

FIG. 8C shows device 200 coupled to a renal artery 220 of a subject 222. When deployed at this location, device 200 provides increased blood flow and/or pressure to a kidney 224, thereby treating kidney conditions caused by poor blood circulation to the kidney. Such conditions include, for example, renal failure and hypertension. Alternatively, device 200 is coupled between an abdominal aorta 226 and renal artery 220 (configuration not shown). In an embodiment of the present invention, device 310, as described hereinbelow with reference to FIGS. 9A and 9B, is placed in abdominal aorta 226, and the end of tube 350 of device 310 is coupled to renal artery 220 (configuration not shown).

Figure 8D:
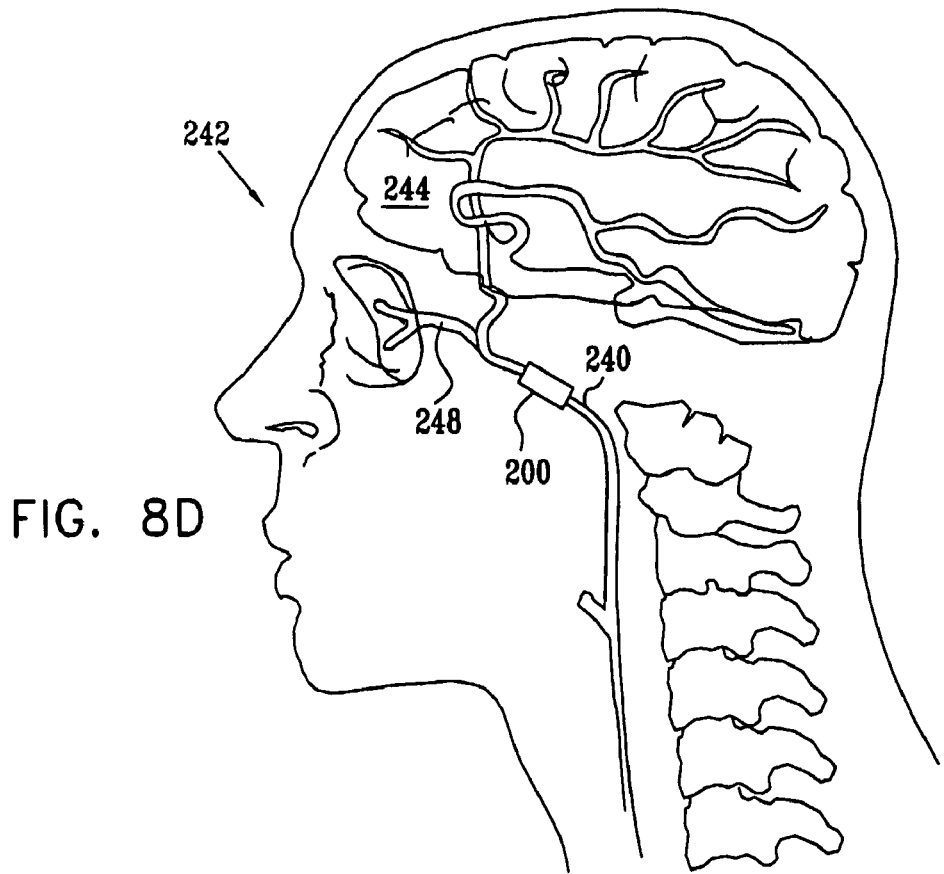

FIG. 8D shows device 200 coupled to an internal carotid artery 240 of a subject 242. When deployed at this location, device 200 provides increased blood flow and/or pressure to portions of a brain 244 of the subject, thereby treating brain conditions caused by poor blood circulation to the brain. Such conditions include, for example, stroke. In addition, when deployed at this location, device 200 provides increased blood flow and/or pressure to a retinal artery via an ophthalmic artery 248, thereby treating eye conditions caused by poor blood circulation to the eye. Such conditions include, for example, retinal vessel occlusion (retinal artery or vein occlusion). Alternatively or additionally, device 200 is coupled directly to ophthalmic artery 248, or to another artery in the head.

Figure 8E:
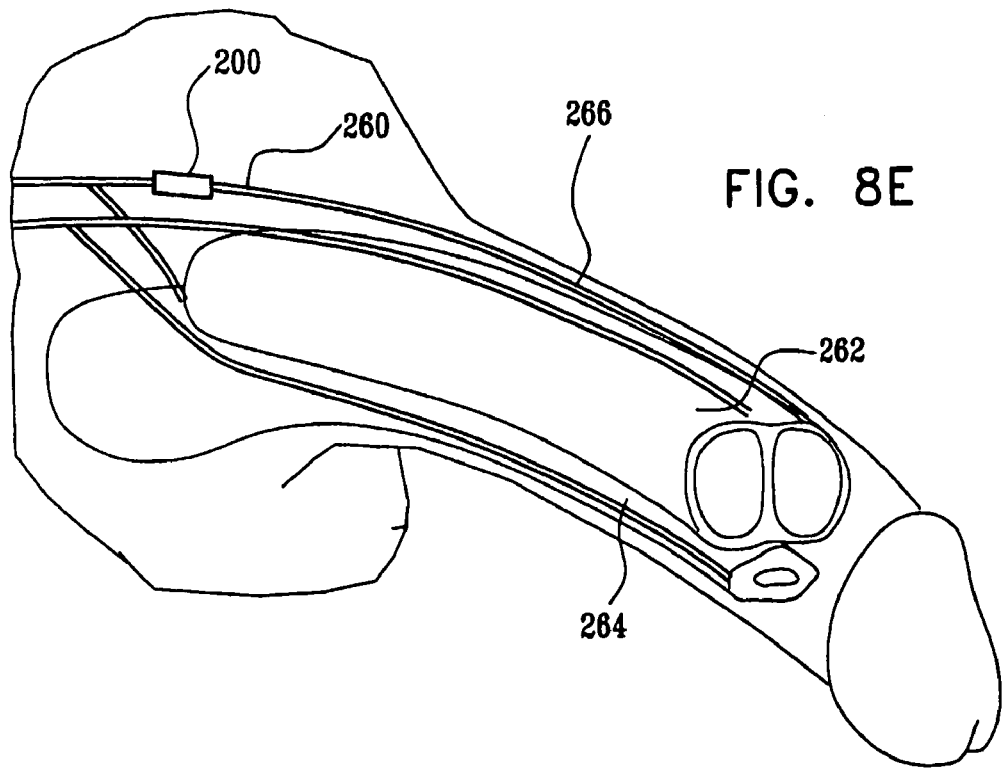

FIG. 8E shows device 200 coupled to a penile artery 260. When deployed at this location, device 200 provides increased blood flow to a corpus cavernosum 262 and/or a corpus spongiosum 264, thereby enabling an erection for subjects suffering from some forms of erectile dysfunction. Alternatively or additionally, device 200 is coupled to a dorsal penile artery 266.

Figure 8F:
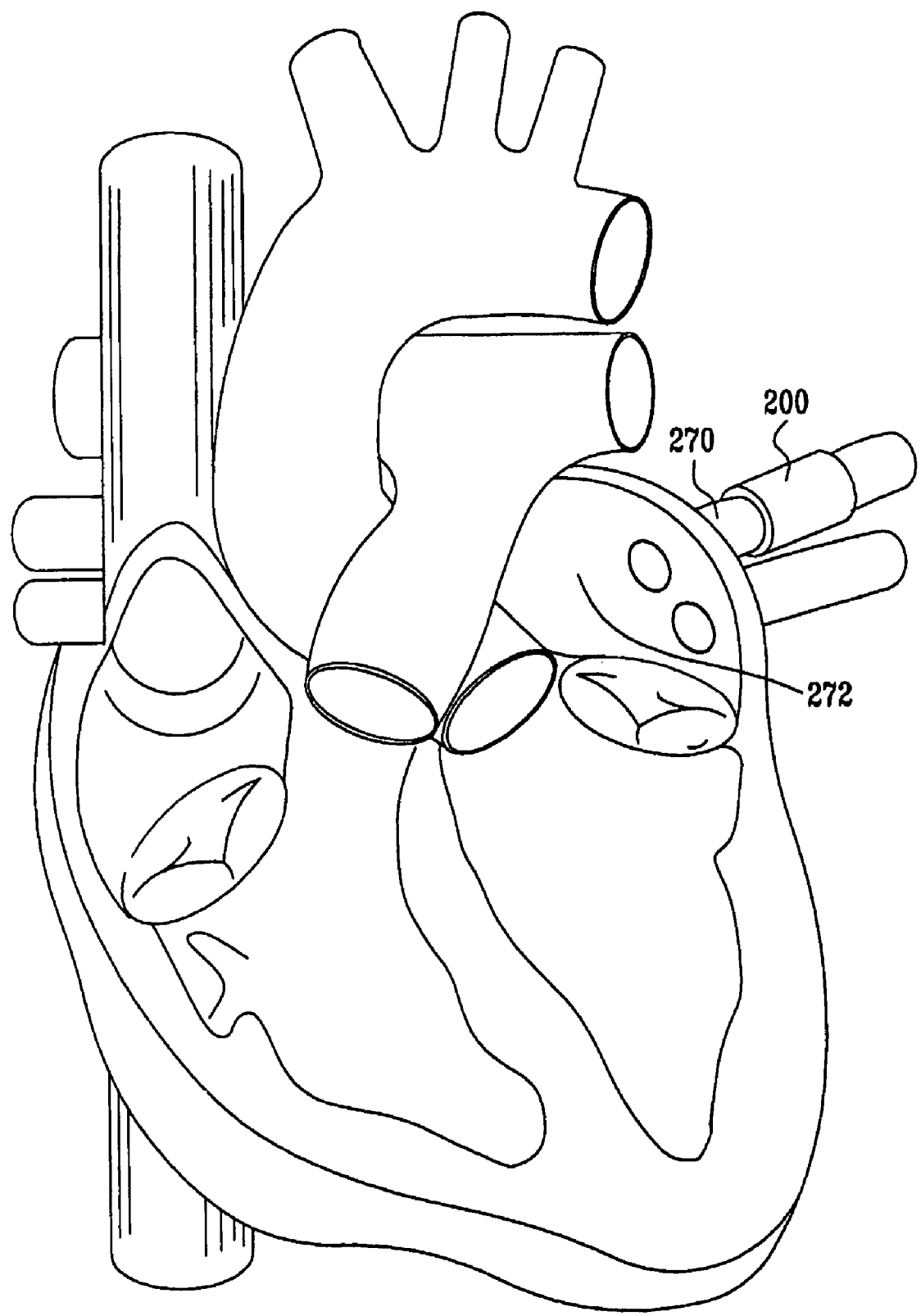

FIG. 8F shows device 200 coupled to a pulmonary vein 270. When deployed at this location, device 200 increases blood flow from one or both of the lungs to a left atrium 272, thereby treating, for example, diastolic heart failure. For some applications, a plurality of devices 200 are coupled to a plurality of pulmonary veins 270 of the subject.

FIGS. 9A and 9B are a pictorial view and a schematic cross-sectional view, respectively, of an extracardiac fully-implantable blood flow amplification device 310, in accordance with an embodiment of the present invention. Device 310 typically has the general shape of an open-ended cylinder or an open-ended wine barrel, and comprises two first flexible chambers 320a and 320b and a second flexible chamber 322, positioned between the two first chambers.

Device 310 is adapted to be placed in an artery of a subject, for example as described hereinbelow with reference to FIGS. 12A and 12B, such that both a first end 326 thereof, adjacent to first chamber 320a, and a second end 328 thereof, adjacent to first chamber 320b, are in fluid communication with blood of the artery. Device 310 typically has an outer diameter D of between about 0.5 and about 1 cm, and a length L of between about 1 and about 10 cm.

A casing 330 of device 310 comprises an outer wall 332, which is typically stiff, and may, for example, comprise a biocompatible metal. Casing 330 also comprises an inner wall 334, which is flexible, and may, for example, comprise a biocompatible metallic membrane. Casing 330 is shaped so as to define a hollow compressible chamber 336 between outer wall 332 and inner wall 334. Compressible chamber 336 typically comprises a gas, such as air, at a pressure of between about 0 and about 100 mm Hg (e.g., 50-80 mm Hg), prior to placement in the subject's body. When blood pressure is applied to inner wall 334, the inner wall deflects towards outer wall 332, compressing the gas and storing the potential energy generated by the force of the blood pressure. Alternatively, casing 330 comprises an elastic material, a spring, or some other means for storing and returning force applied to the inside surface of the casing. Second chamber 322 is typically positioned such that an outer surface 338 thereof is in mechanical contact with inner wall 334 of casing 330. Although casing 330 is shown with respect to outer surface 338 as being generally concave in geometry, the casing may have other geometries, such as a straight or a convex geometry.

Typically, outer surface 338 of second chamber 322 has a surface area less than about 50% of a surface area of inner wall 334 of casing 330, such as between about 30% and about 40% of the surface area of inner wall 334, or, for some applications, between about 10% and about 30% of the surface area of inner wall 334. Depending upon the specific therapeutic application, the surface area of outer surface 338 of second chamber 322 is typically between about 2.5 and about 7.5 cm$^2$, and the surface area of inner wall 334 of casing 330 is typically between about 5 and about 15 cm$^2$. Also depending upon the specific therapeutic application, the combined volume of first chambers 320a and 320b is typically between about 10 and about 20 ml, and the volume of second chamber 322 is typically between about 5 and about 10 ml.

Although outer surface 338 of second chamber 322 is shown as being in close contact with inner wall 334 of casing 330, for some applications at least a portion of outer surface 338 is not fixed to casing 330. In this manner, during at least some cardiac phases, outer surface 338 may separate from casing 330, causing first chambers 320a and 320b to be in direct fluid communication with one another around outer surface 338, and facilitating a small amount of blood flow between chambers 320a and 320b. Alternatively or additionally, outer surface 338 of second chamber 322 and/or inner wall 334 of casing 330 is shaped so as to define one or more channels between outer surface 338 and inner wall 334, so as to allow a small amount of blood to flow through the channels between first chambers 320a and 320b. In either case, such blood flow may reduce the likelihood of the occurrence of any potential blood coagulation in device 310.

Second chamber 322 comprises a pressure-sensitive valve 346, positioned at an opening 348 between second chamber 322 and first chamber 320a. Device 310 comprises a tube 350, coupled to an opening 352 defined by second chamber 322 on a surface thereof typically, but not necessarily, opposite opening 348. Tube 350 typically passes through first chamber 320b and second end 328, and out of device 310, without being in fluid communication with blood in first chamber 320b. Alternatively, opening 352 is defined by second chamber 322 on the surface thereof that defines opening 348, and tube 350 passes through first chamber 320a and first end 326, and out of device 310 without being in fluid communication with blood in first chamber 320a (configuration not shown). An open end of tube 350 (not shown) is coupled to tissue of the subject in need of additional blood perfusion, for example as described hereinbelow with reference to FIGS. 12A and 12B. For some applications, at least a portion of tube 350 comprises human or animal graft material, such as a human or animal artery.

Figure 10A:
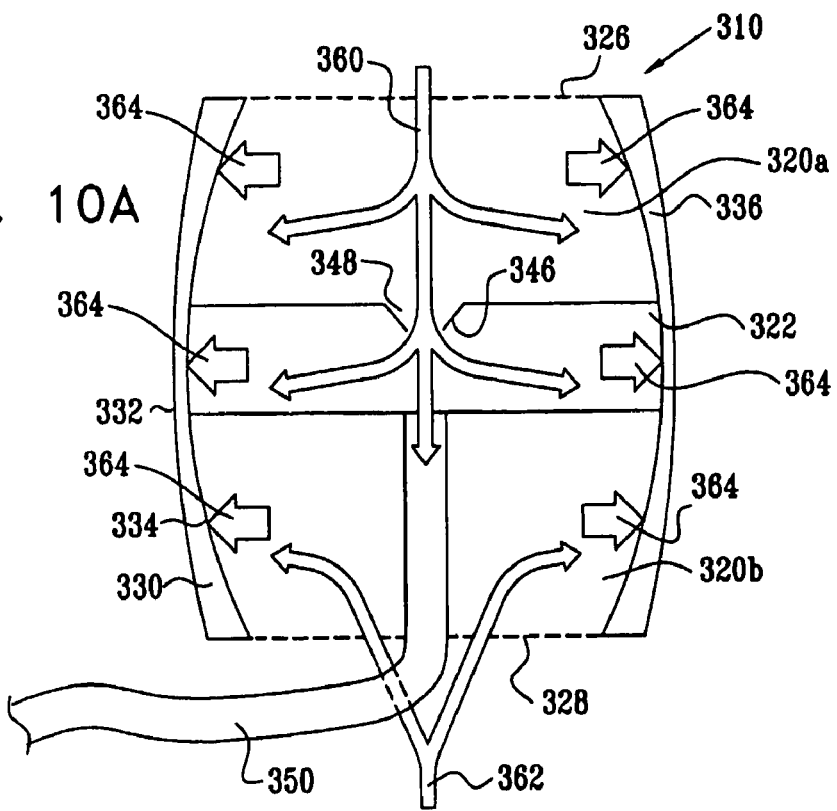
FIGS. 10A and 10B are schematic cross-sectional views of the device of FIGS. 9A and 9B during systole and diastole, respectively, in accordance with an embodiment of the present invention.
Figure 10B:
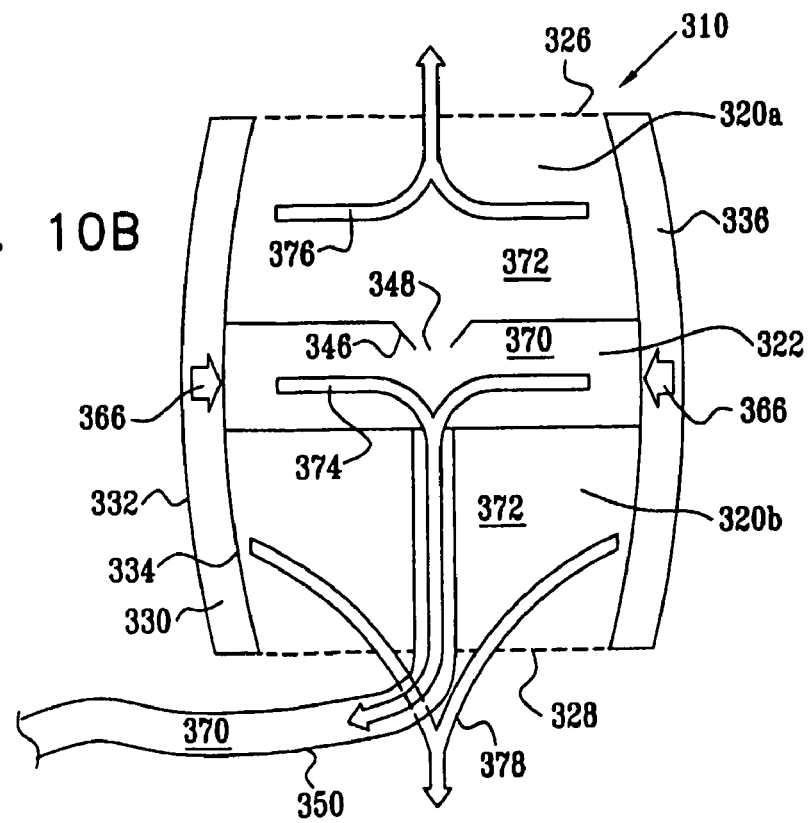

FIGS. 10A and 10B are schematic cross-sectional views of device 310 during systole and diastole, respectively, in accordance with an embodiment of the present invention. During a systolic phase of operation of device 310, as shown in FIG. 10A, valve 346 opens and blood: (a) enters first chamber 320a, second chamber 322, and tube 350, as symbolically represented by an arrow 360, and (b) enters first chamber 320b, as symbolically represented by an arrow 362. The blood expands first chambers 320a and 320b and second chamber 322 in the direction indicated by arrows 364, applying systolic blood pressure to inner wall 334 of casing 330. Inner wall 334 deflects towards outer wall 332, compressing the gas contained in casing 330, thereby storing potential energy therein. Valve 346 is typically in an open position only when a pressure gradient thereacross is greater than a threshold value, e.g., greater than between about 1 and about 4 mm Hg.

During a subsequent diastolic phase of operation, as shown in FIG. 10B, valve 346 closes, and inner wall 334 applies the stored potential energy to both first chambers 320a and 320b and second chamber 322, contracting the chambers in the direction indicated by arrows 366. For the purposes of the description hereinbelow, two volumes of blood are described: (a) "pressurized" blood 370, comprising the blood in second chamber 322 and tube 350, and (b) "upstream" blood 372, comprising the blood in first chambers 320a and 320b and the artery. During diastole, the resistance to movement of pressurized blood 370 out of device 310 is substantially greater than the resistance to movement of upstream blood 372 out of device 310. Inner wall 334 applies a disproportionately large portion of the stored potential energy to second chamber 322. Correspondingly, the force applied to second chamber 322 generates a pressure in pressurized blood 370 that is greater than diastolic blood pressure in the artery, and is typically greater than systolic blood pressure in the artery. As a result, device 310 drives pressurized blood 370 through tube 350 at high pressure, as indicated symbolically by arrow 374, and also drives upstream blood 372 out of first chambers 320a and 320b through first end 326 and second end 328, respectively, at lower pressure, as indicated symbolically by arrows 376 and 378, respectively. Device 310 thus provides increased blood circulation to tissue in a vicinity of the open end of tube 350, thereby treating conditions caused by insufficient blood circulation, such as those described hereinbelow with reference to FIGS. 12A, 12B, and 17.

For some applications, device 310 comprises a volume adjustment mechanism similar to mechanism 80 described hereinabove with reference to FIG. 4 (configuration not shown), mutatis mutandis. Alternatively or additionally, for some applications device 310 comprises a pressure adjustment mechanism, similar to mechanism 90 described hereinabove with reference to FIG. 5 (configuration not shown), mutatis mutandis.

Figure 11A:
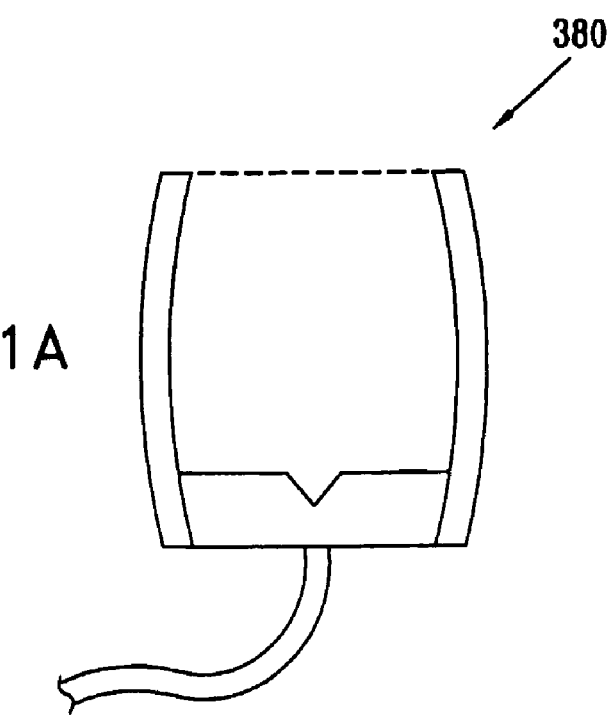
FIGS. 11A and 11B are schematic cross-sectional views of still other blood flow amplification devices, in accordance with embodiments of the present invention.
Figure 11B:
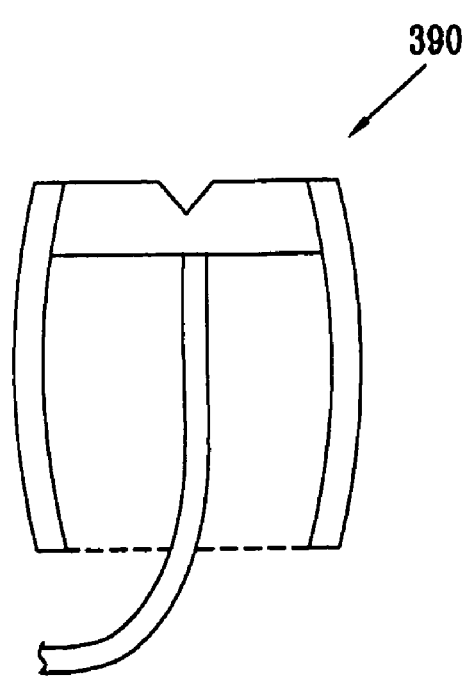

FIGS. 11A and 11B are schematic cross-sectional views of extracardiac fully-implantable blood flow amplification devices 380 and 390, respectively, in accordance with embodiments of the present invention. Device 380 is substantially the same as device 310, described hereinabove with reference to FIGS. 9A and 9B, except that device 380 lacks first chamber 320b of device 310. Device 390 is substantially the same as device 310, except that device 390 lacks first chamber 320a of device 310. Operation of devices 380 and 390 is similar to that of device 310, although the pressure of the blood expelled through the tube may be lower for devices 380 and 390 than for device 310, for some applications.

Figure 12A:
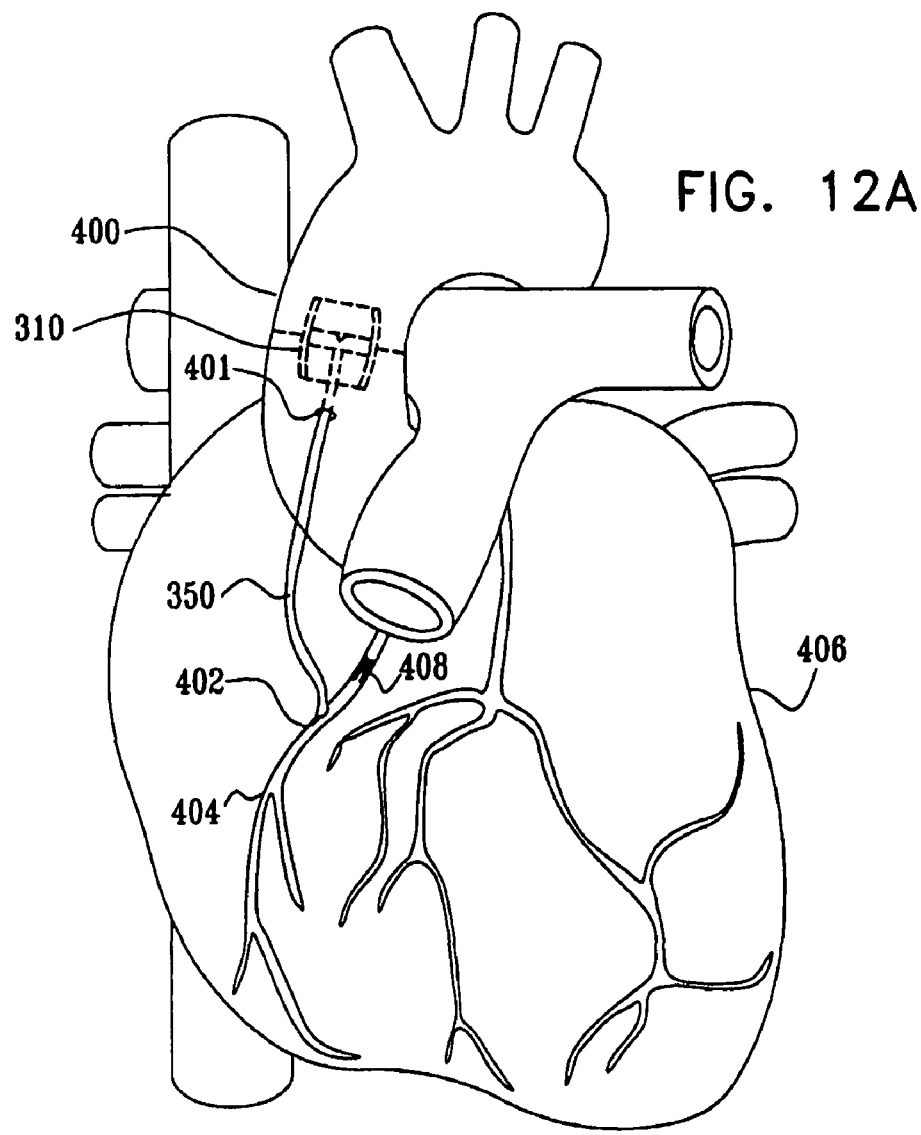
FIGS. 12A and 12B are schematic pictorial illustrations of the use of the device of FIGS. 9A and 9B to treat cardiac conditions, in accordance with embodiments of the present invention.

FIG. 12A is a schematic pictorial illustration of the use of device 310 to treat some cardiac conditions, in accordance with an embodiment of the present invention. FIG. 12A shows device 310 placed in an ascending aorta 400. Tube 350 passes through an opening 401 in ascending aorta 400, which opening has been surgically sealed around the tube. An end 402 of tube 350 is coupled to a coronary artery 404 of a heart 406, thereby bypassing an obstructed area 408 of coronary artery 404. Alternatively, end 402 is coupled to a bypass graft supplying blood to coronary artery 404 (configuration not shown). Tube 350 provides increased blood flow and/or pressure to coronary artery 404, and typically reestablishes sufficient blood flow in the occluded artery, treating conditions such as angina and myocardial infarction.

Figure 12B:
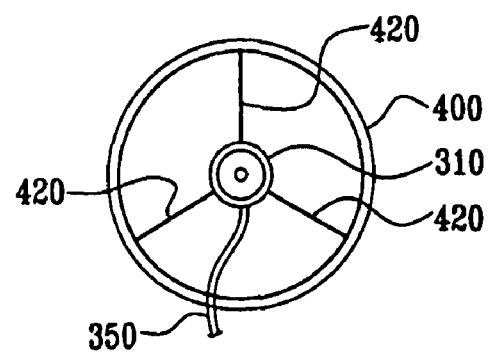

FIG. 12B is a schematic cross-sectional illustration of device 310 placed in ascending aorta 400, in accordance with an embodiment of the present invention. In this embodiment, device 310 is held in place by a stent 420 placed in ascending aorta 400, such that blood is able to flow around device 310.

Figure 13:
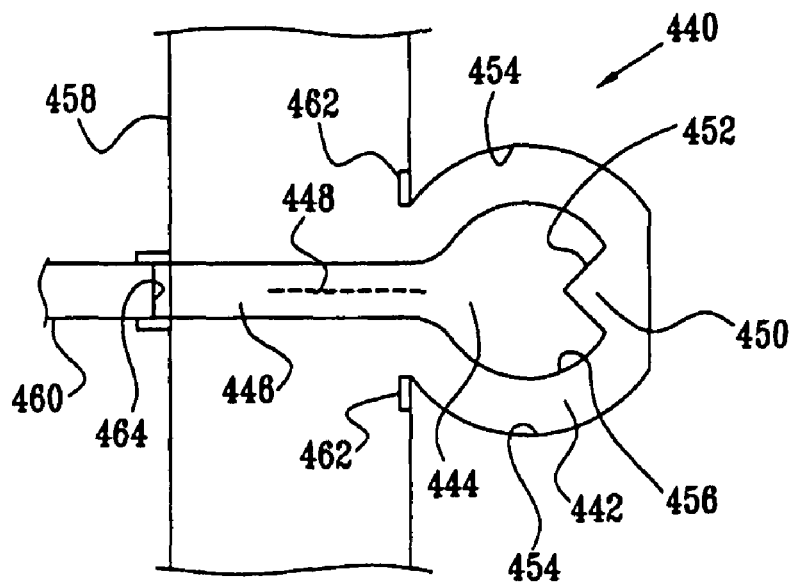
FIG. 13 is a schematic cross-sectional view of another blood flow amplification device, in accordance with an embodiment of the present invention.

FIG. 13 is a schematic cross-sectional view of an extracardiac fully-implantable blood flow amplification device 440, in accordance with an embodiment of the present invention. Device 440 comprises a first flexible chamber 442, a second flexible chamber 444, and a lumen 446. First flexible chamber 442 typically but not necessarily surrounds second flexible chamber 444, and both chambers are typically substantially radially symmetrical around a longitudinal axis 448. Second chamber 444 is shaped so as to define an opening 450 between second chamber 444 and first chamber 442, at which opening second chamber 444 comprises a pressure-sensitive valve 452. First chamber 442 typically has a volume of between about 3 and about 10 ml, and second chamber 444 typically has a volume of between about 1 and about 5 ml. For some applications, at least a portion of lumen 446 comprises human or animal graft material, such as a human or animal artery.

First chamber 442 defines an elastic first surface 454, and second chamber 444 defines a second surface 456, which is flexible but not necessarily elastic. Alternatively, first surface 454 is not necessarily elastic, and a spring external to first surface 454 is positioned to provide elasticity to the surface (configuration not shown).

Device 440 is typically adapted to be coupled to an ascending aorta 458 and to a coronary artery 460. Alternatively, device 440 is adapted to be coupled to another primary artery and another secondary artery that branches off of the primary artery, such as to an abdominal aorta and a renal artery, respectively. Device 440 is typically inserted into aorta 458 using a transcatheter approach. Chambers 442 and 444 are passed out of the aorta through an opening created in the side of the aorta, such that the chambers are positioned immediately outside the aorta. The chambers are coupled to the aorta using coupling means 462, which will be evident to those skilled in the art, having read the present application. For some applications, coupling means 462 comprise suture and/ or adhesive. Lumen 446 remains extended across at least a portion of the aorta, and an end 464 thereof is coupled to coronary artery 460, for example, by being inserted therein.

During a systolic phase of operation of device 440, valve 452 opens and blood enters first chamber 442 and second chamber 444. The blood expands both chambers, applying systolic blood pressure to elastic first surface 454, which expands, thereby storing potential energy therein. During a subsequent diastolic phase of operation, valve 452 closes, and elastic first surface 454 applies the stored potential energy to both first chamber 442 and second chamber 444, thereby contracting the chambers. The force applied to second chamber 444 generates a pressure in the blood stored therein, which ejects the blood through lumen 446 and into coronary artery 460, typically at a higher pressure than would occur during systole in the absence of device 440. Device 440 thus provides increased blood circulation to coronary artery 460, thereby treating conditions caused by insufficient blood circulation, such as some cardiac conditions.

Figure 14:
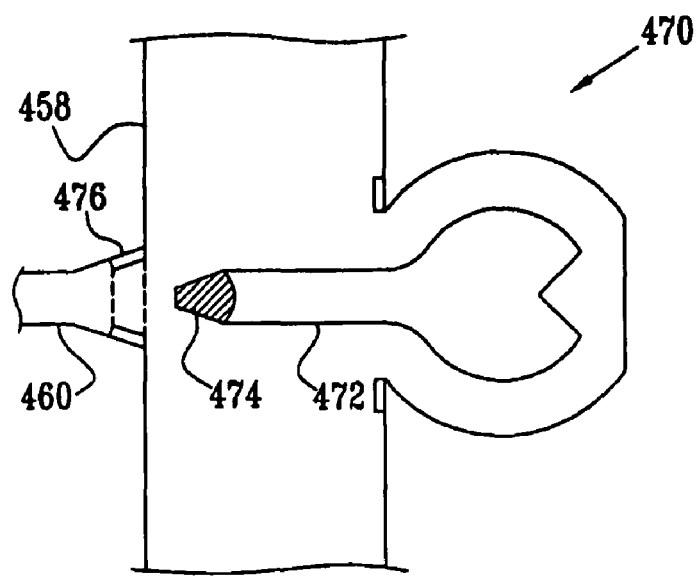
FIG. 14 is a schematic cross-sectional view of yet another blood flow amplification device, in accordance with an embodiment of the present invention.

FIG. 14 is a schematic cross-sectional view of an extracardiac fully-implantable blood flow amplification device 470, in accordance with an embodiment of the present invention. Except as described below, device 470 is generally similar to device 440, described hereinabove with respect to FIG. 13. Rather than being coupled directly to coronary artery 460, a lumen 472 of device 470 typically comprises a nozzle 474, which is positioned within aorta 458 in a vicinity of coronary artery 460, and oriented so as to direct blood ejected from the nozzle towards the coronary artery. An inlet 476, e.g., comprising a stent, is typically implanted at the junction of coronary artery 460 with aorta 458, so as to increase uptake of blood by the coronary artery from the nozzle.

Figure 15A:
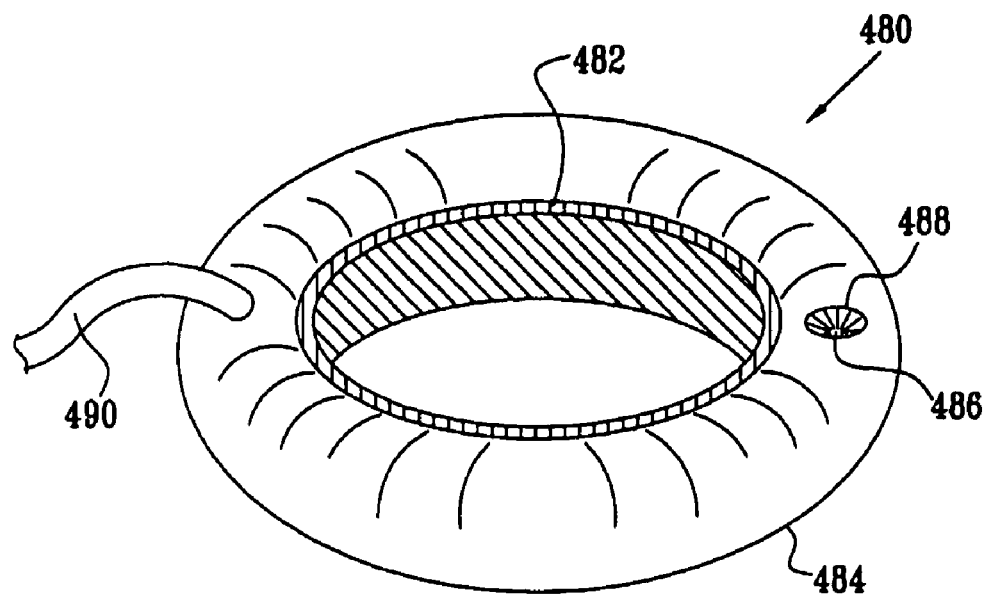
FIGS. 15A and 15B are a pictorial view and a schematic cross-sectional view, respectively, of still another blood flow amplification device, in accordance with an embodiment of the present invention.
Figure 15B:
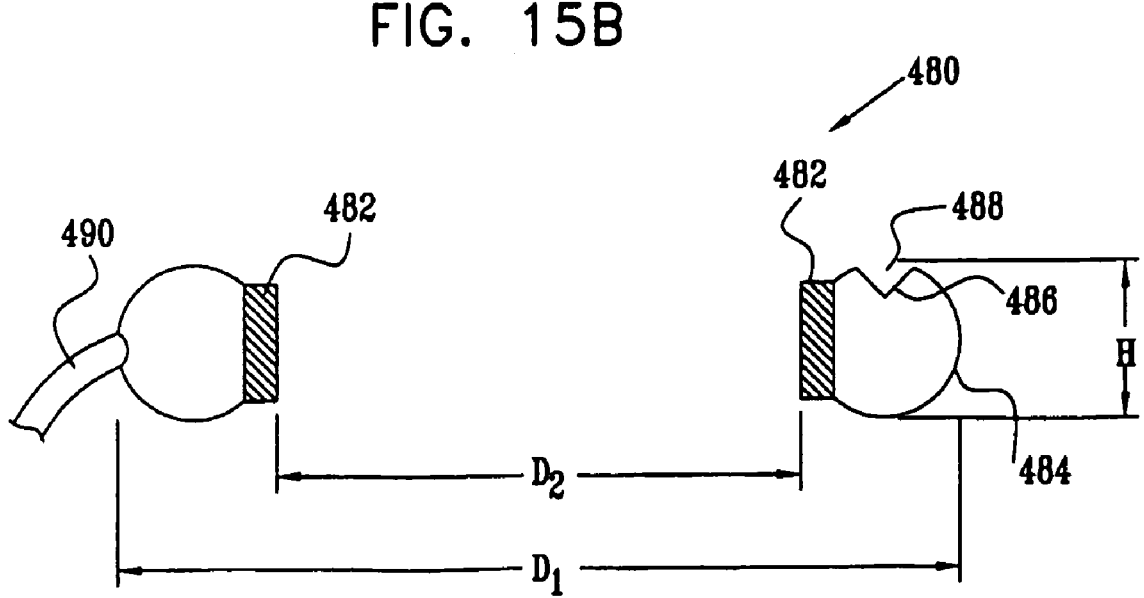

FIGS. 15A and 15B are a pictorial view and a schematic cross-sectional view, respectively, of an extracardiac fully-implantable blood flow amplification device 480, in accordance with an embodiment of the present invention. Device 480 comprises a generally circular, substantially stiff inner ring 482, around which is coupled a toroid-shaped flexible bladder 484. Device 480 is adapted to be placed in and secured in place in an artery, such as an ascending aorta.

Bladder 484 comprises a pressure-sensitive valve 486, positioned at an opening 488 defined by the outer surface of the bladder. Device 480 comprises a tube 490, coupled to bladder 484. An open end of tube 490 (not shown) is coupled to tissue of the subject in need of additional blood perfusion, for example a coronary artery. For some applications, at least a portion of tube 490 comprises human or animal graft material, such as a human or animal artery.

Figure 16A:
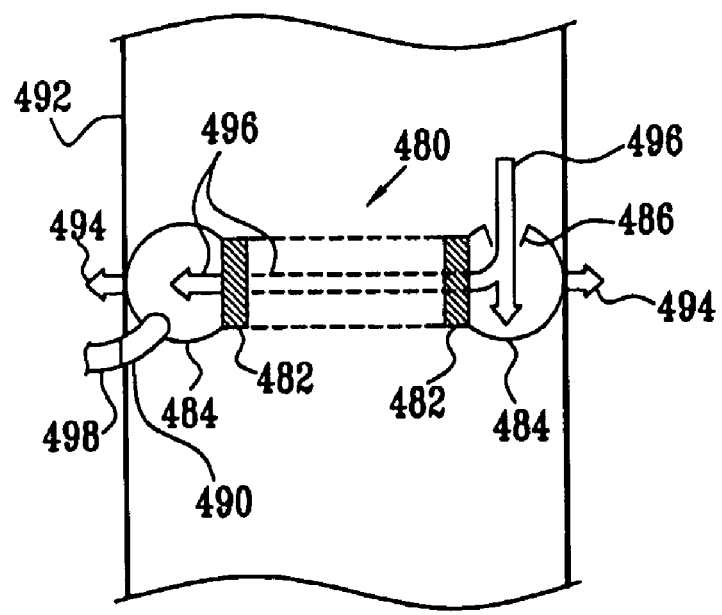
FIGS. 16A and 16B are schematic cross-sectional views of the device of FIGS. 15A and 15B during systole and diastole, respectively, in accordance with an embodiment of the present invention.
Figure 16B:
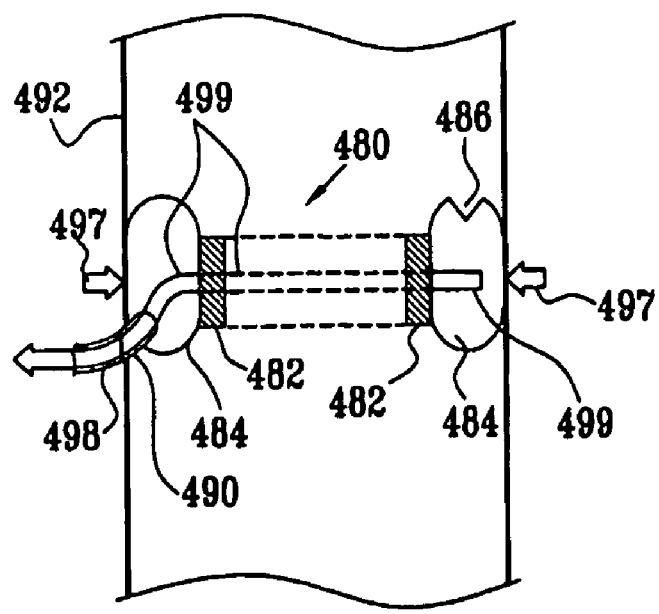

FIGS. 16A and 16B are schematic cross-sectional views of device 480 during systole and diastole, respectively, in accordance with an embodiment of the present invention. During a systolic phase of operation of device 480, as shown in FIG. 16A, a primary artery 492, in which device 480 has been placed, dilates, as indicated by arrows 494. At essentially the same time, valve 486 opens and blood, driven by systolic pressure, enters bladder 484, as symbolically represented by an arrow 496.

During a subsequent diastolic phase of operation, as shown in FIG. 16B, valve 486 substantially closes, and primary artery 492 constricts, as indicated by arrows 497, ejecting blood, as symbolically represented by an arrow 499, from bladder 484 into tube 490, and therethrough into a secondary artery 498 to which tube 490 is coupled. The blood ejected through tube 490 is typically at a higher pressure than would occur during systole in the absence of device 480. Device 480 thus provides increased blood circulation to secondary artery 498, thereby treating conditions caused by insufficient blood circulation.

For some applications, primary artery 492 includes the ascending aorta, and secondary artery 498 includes a coronary artery.

Figure 17:
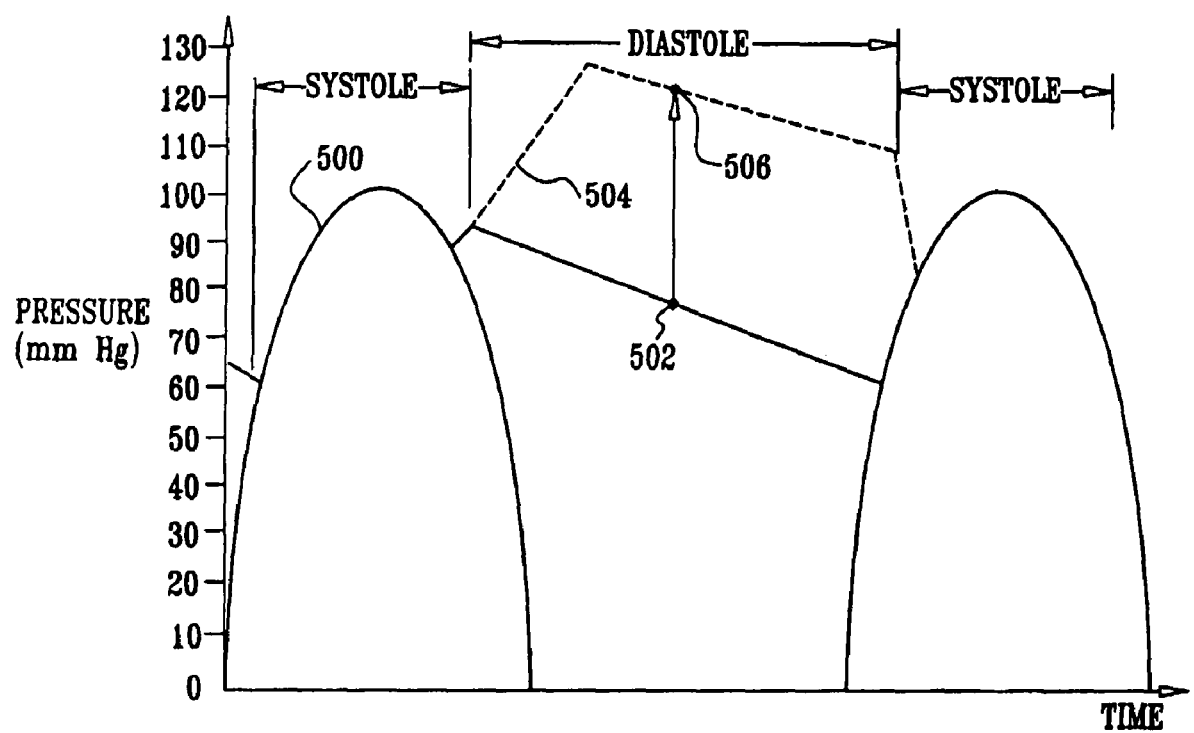
FIG. 17 is a graph showing example aortic pressure curves without treatment and during treatment with a blood flow amplification device, in accordance with an embodiment of the present invention.

FIG. 17 is a graph showing example aortic pressure curves without treatment and during treatment with an extracardiac fully-implantable blood flow amplification device, such as device 10, device 110, device 310, device 440, or device 480, in accordance with an embodiment of the present invention. It is emphasized that these pressure curves are exemplary, and reflect assumptions regarding a particular configuration of the blood flow amplification device and a theoretical subject's reactions to the device. In actual human use, physiological responses are expected to vary substantially from subject to subject, in part dependent upon the particular configuration of the device.

A curve 500 represents aortic blood pressure without treatment with the blood flow amplification device. A point 502 on curve 500 indicates the approximate point during diastole at which the aorta begins to supply substantial blood flow to a conventional coronary bypass graft between the aorta and a coronary artery or a branch of a coronary artery. As can be seen, by this point aortic blood pressure has dropped substantially from its peak. Such lower pressure is sometimes insufficient to supply an adequate blood supply to the occluded coronary artery via the graft.

A curve 504 represents blood pressure output by the blood flow amplification device during treatment therewith. As can be seen, at a point 506 during diastole at which the device supplies blood to the occluded coronary artery, substantially higher pressure is available to provide blood flow to the coronary artery.

It is noted that the increased blood pressure illustrated by curve 504 occurs only in the blood output from the blood flow amplification device, and not in aortic blood generally. The quantity of blood supplied by the device to the coronary artery generally represents less than 5% of the total output of the heart, so heart muscle work used to increase the pressure of this blood only minimally affects the remainder of the circulatory system.

In general, curves similar to curves 500 and 504 result from treatment by the blood flow amplification device of peripheral arteries, albeit at lower untreated and treated pressures.

Figure 18A:
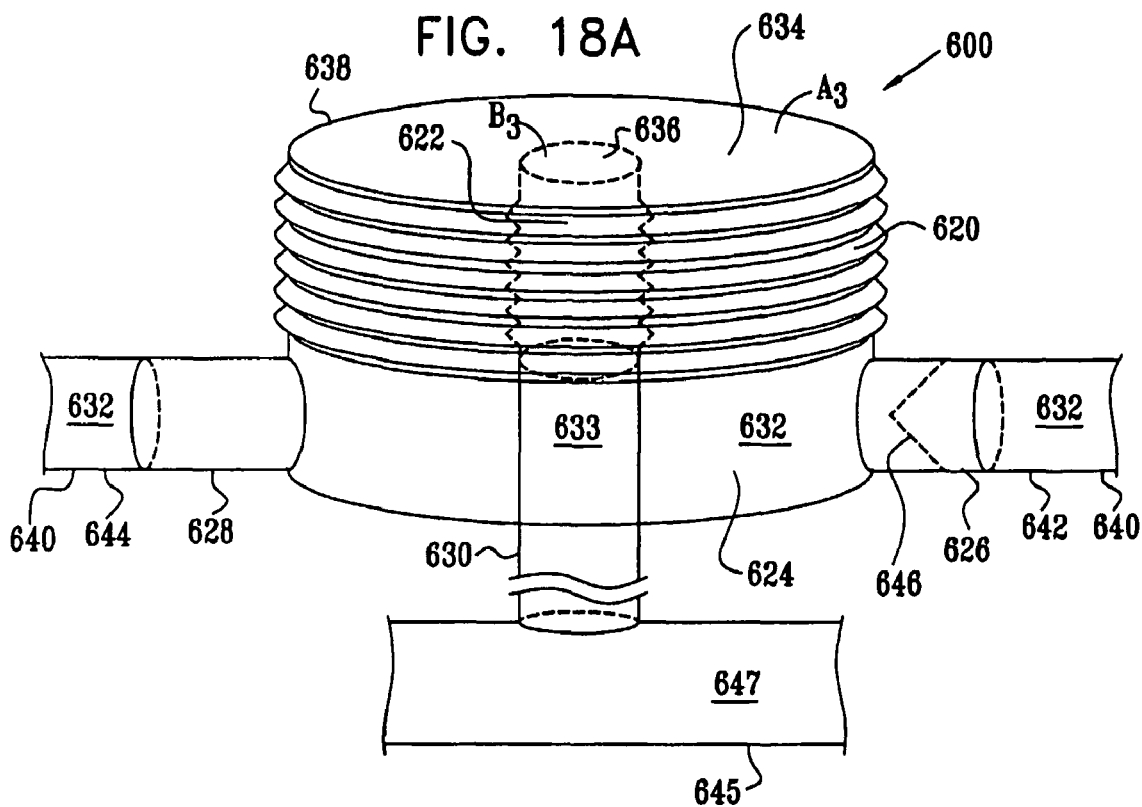
FIGS. 18A and 18B are a pictorial view and a schematic cross-sectional view, respectively, of yet another blood flow amplification device, in accordance with an embodiment of the present invention.
Figure 18B:
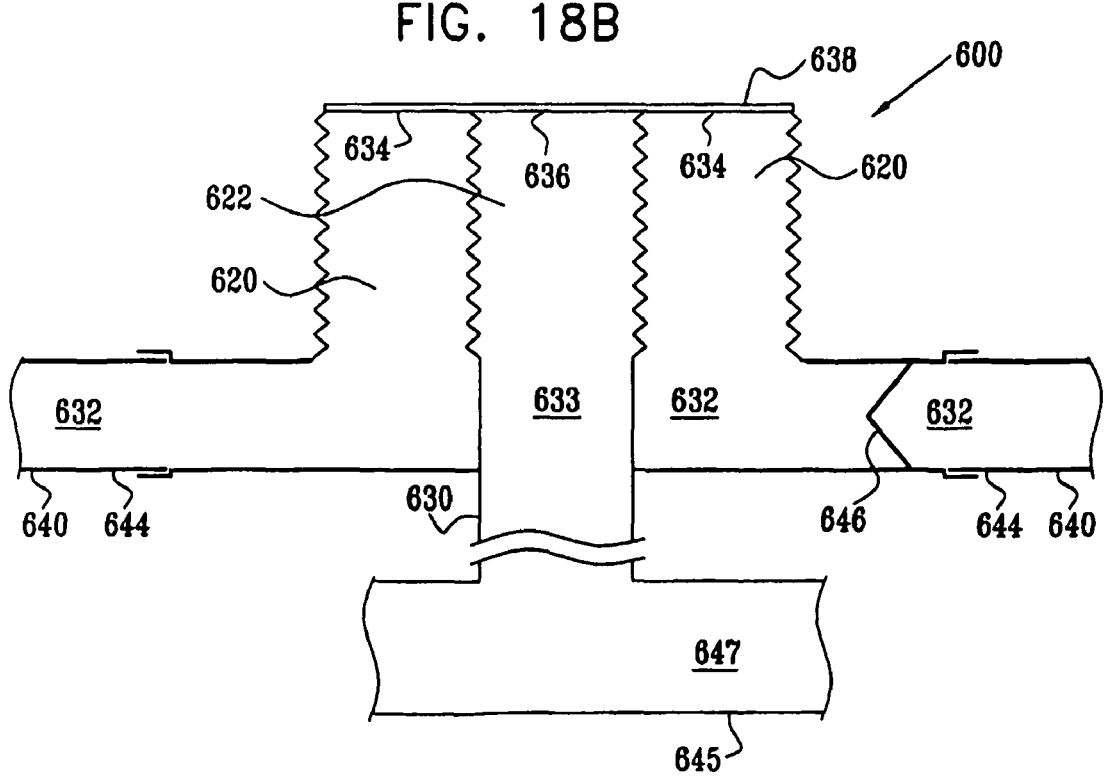

FIGS. 18A and 18B are a pictorial view and a schematic cross-sectional view, respectively, of an extracardiac fully-implantable blood flow amplification device 600, in accordance with an embodiment of the present invention. Device 600 comprises a first flexible chamber 620, a second flexible chamber 622, and a base chamber 624 in fluid communication with first chamber 620. Device 600 further comprises (a) an inflow conduit 626 and an outflow conduit 628, both of which are coupled to and in fluid communication with base chamber 624, and (b) a pressure conduit 630, in fluid communication with second chamber 622. Optionally, second chamber 622 and base chamber 624 are an integrated unit (configuration not shown).

Device 600 is adapted to be coupled to a blood vessel 640 of a subject, by coupling inflow conduit 626 to a first site 642 of the blood vessel, and outflow conduit 628 to a second site 644 of the blood vessel, the second site distal to the first site with respect to blood circulation, so that blood 632 enters the device from the blood vessel. Pressure conduit 630 is adapted to be coupled to an artery 645 of the subject, such that a pressure-transmitting fluid 633 is in pressure communication with blood 647 of artery 645. For some applications, as shown in FIGS. 18A and 18B, pressure conduit 630 is coupled to artery 645, e.g., by anastomosis, such that the interior of the conduit is in fluid communication with arterial blood 647; in these applications arterial blood 647 serves as pressure-transmitting fluid 633. For other applications, such as described hereinbelow with reference to FIGS. 20A, 20B, and 20C, a membrane or other pressure-transfer mechanism separates the interior of pressure conduit 630 from arterial blood 647; in these applications pressure-transmitting fluid 633 typically comprises a biocompatible fluid, such as saline solution.

In the embodiment shown in FIGS. 18A and 18B, the first and second chambers are generally cylindrically shaped, and second chamber 622 is shown surrounded by first chamber 620. Alternatively, the chambers have different shapes, and/or first chamber 620 and second chamber 622 are arranged side-by-side, or in another arrangement (configurations not shown).

First chamber 620 and second chamber 622 define a first surface 634 and a second surface 636, respectively, each of which surfaces is in mechanical communication with a common surface 638 that applies an elastically-derived force. For some applications, first surface 634 and second surface 636 together comprise surface 638. Surface 638 is adapted to facilitate storage, as potential energy, of the work applied thereto by first surface 634 and second surface 636. Surface 638 is substantially identical to surface 38, described hereinabove with reference to FIGS. 1A, 1B, and 2, and utilizes the same sources of the elastically-derived force as described with respect to surface 38 (e.g., springs having various configurations).

Typically, first surface 634 has a surface area $A_3$, and second surface 636 has a surface area $B_3$, which is less than $A_3$. For example, $B_3$ may be between about 60% and about 80% of $A_3$, or, for some applications, between about 30% and about 60% of $A_3$. Depending upon the specific therapeutic application, $A_3$ is typically between about 4 and about 10 cm$^2$, and $B_3$ is typically between about 1 and about 5 cm$^2$. Also depending upon the specific therapeutic application, the volume of first chamber 620 is typically between about 6 and about 20 ml, and the volume of second chamber 622 is typically between about 3 and about 10 ml. For some applications, the volume of second chamber 622 is between about 25% and about 80% of the volume of first chamber 620.

Device 600 comprises a pressure-sensitive valve 646, positioned within inflow conduit 626 or between the inflow conduit and base chamber 624. Alternatively, valve 646 is not integrated with the rest of device 600, and is instead implanted in blood vessel 640 in a vicinity of first site 642 of the blood vessel (configuration not shown). Valve 646 is configured to bias blood flow in the direction from first site 642 to base chamber 624. Valve 646 is typically in an open position only when a pressure gradient thereacross is greater than a threshold value, e.g., greater than between about 1 and about 4 mm Hg.

Figure 19A:
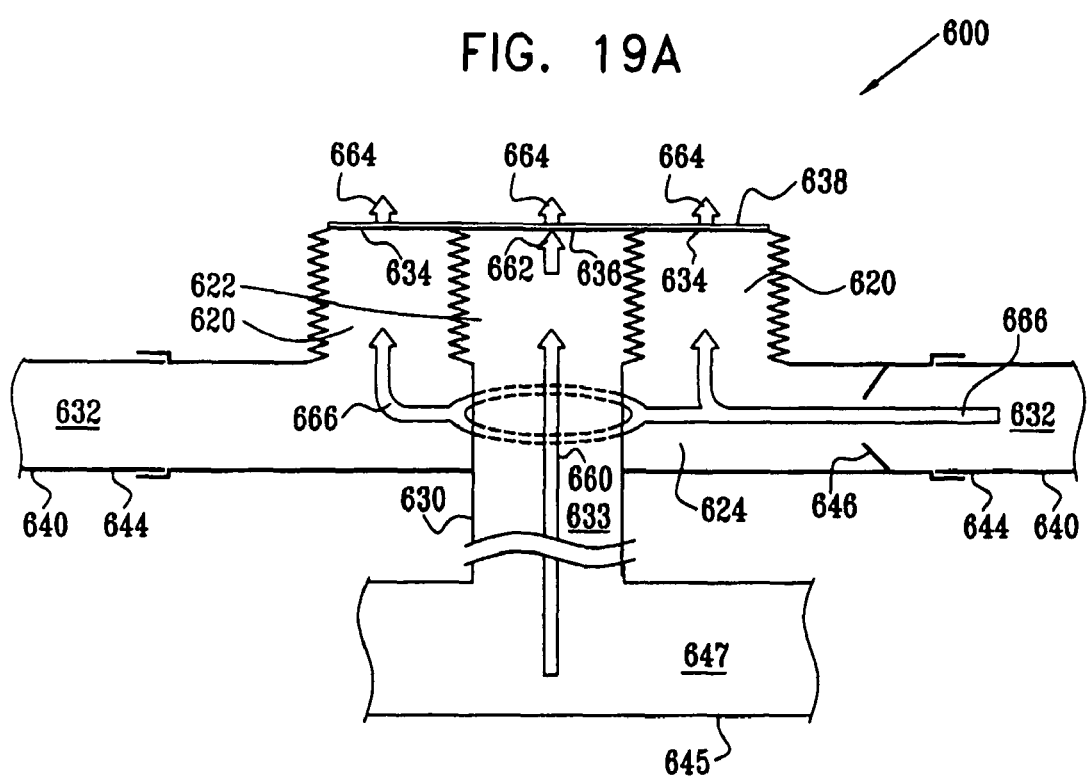
FIGS. 19A and 19B are schematic cross-sectional views of the device of FIGS. 18A and 18B during systole and diastole, respectively, in accordance with an embodiment of the present invention.
Figure 19B:
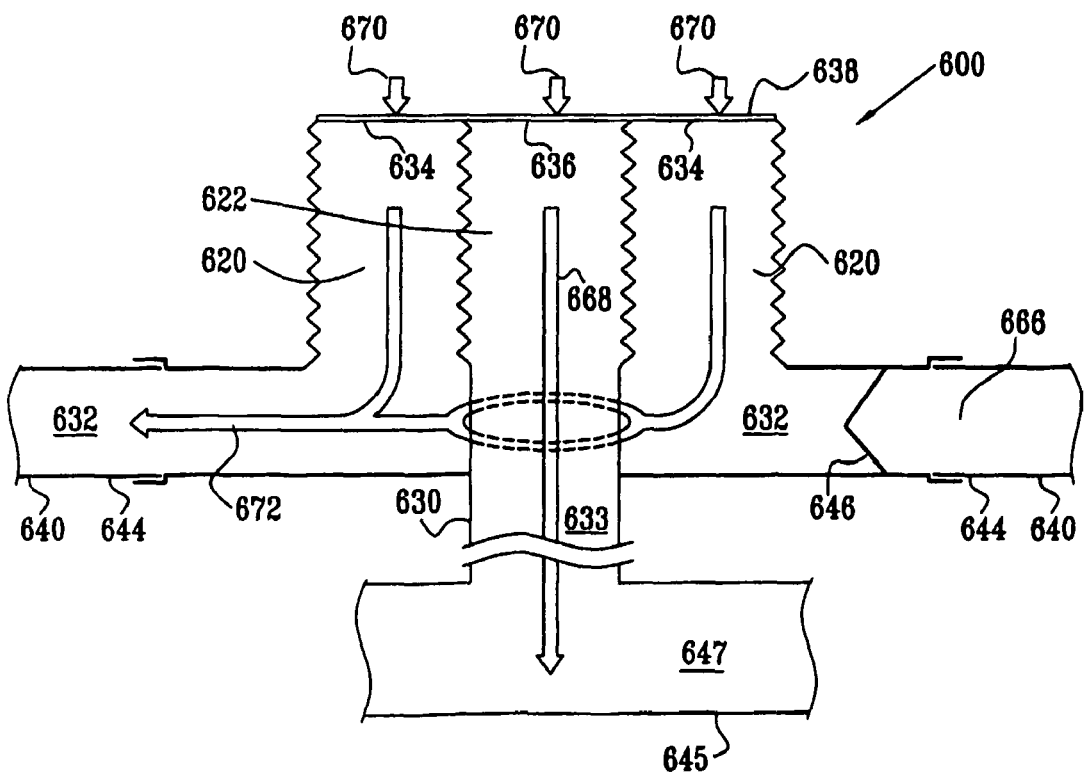

FIGS. 19A and 19B are schematic cross-sectional views of device 600 during systole and diastole, respectively, in accordance with an embodiment of the present invention. During a systolic phase of operation of device 600, as shown in FIG. 19A, the increased systolic pressure of arterial blood 647 is communicated to pressure-transmitting fluid 633, as symbolically represented by an arrow 660. This increased pressure is applied to second surface 636, expanding second chamber 622 in the direction indicated by an arrow 662. As a result, surface 638 moves in the direction indicated by arrows 664, thereby storing potential energy in the source of the elastically-derived force. The motion of surface 638 expands first chamber 620, opening valve 646 and drawing blood 632 into first chamber 620 and base chamber 624, as indicated by an arrow 666.

During a subsequent diastolic phase of operation, as shown in FIG. 19B, the decreased diastolic pressure of arterial blood 647 is communicated to pressure-transmitting fluid 633, as symbolically represented by an arrow 668, resulting in lower pressure in second chamber 622. Surface 638 converts the stored potential energy to kinetic energy, applying a force to both first surface 634 and second surface 636, thereby contracting the chambers in the direction indicated by arrows 670. Valve 646 closes, and first chamber 620 expels blood 632 in the direction indicated by an arrow 672. Device 600 thus increases blood flow through blood vessel 640.

For some applications, device 600 comprises volume adjustment mechanism 80, as described hereinabove with reference to FIG. 4, mutatis mutandis. Alternatively or additionally, for some applications device 600 comprises pressure adjustment mechanism 90, as described hereinabove with reference to FIG. 5, mutatis mutandis.

Figure 20A:
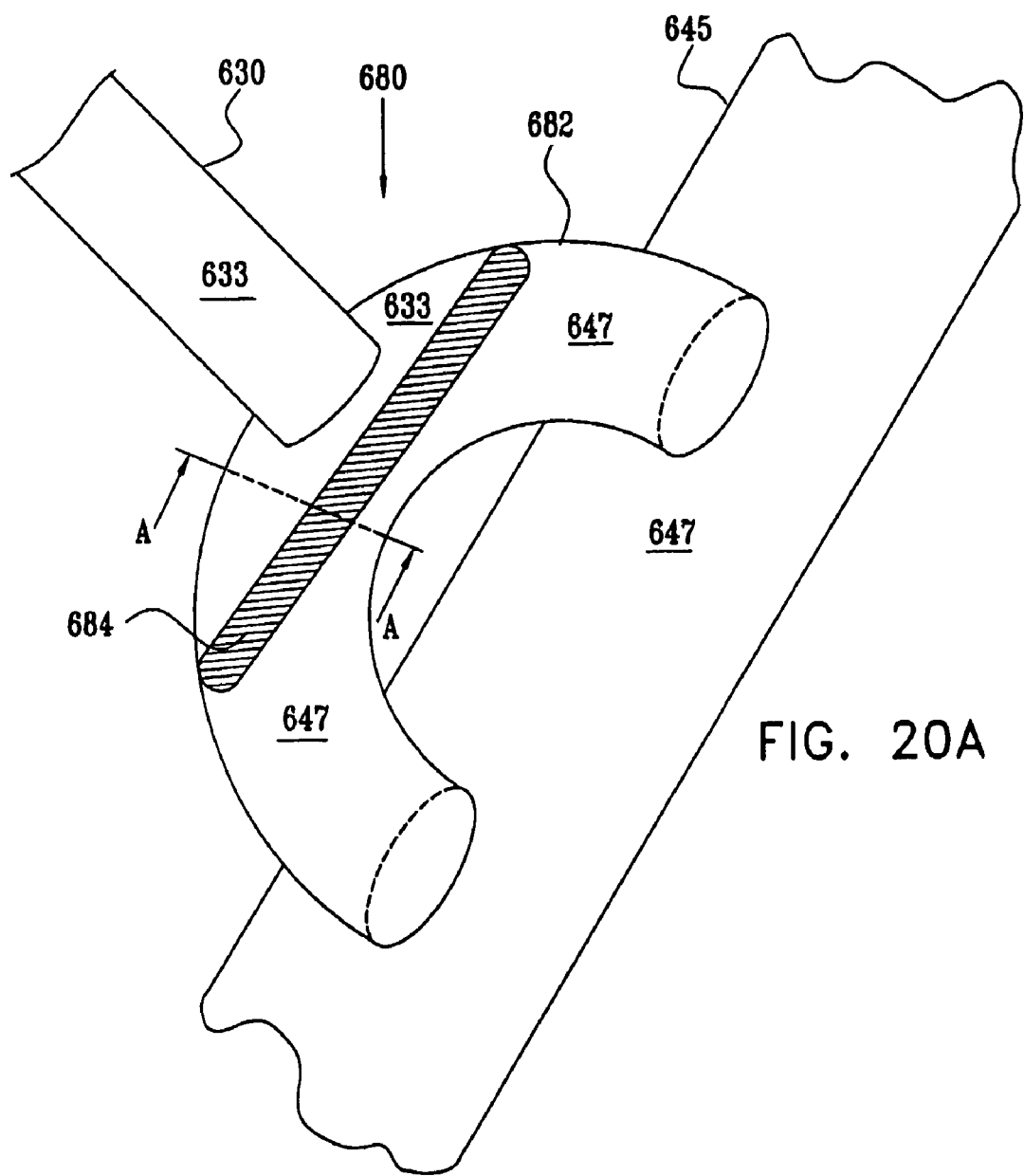
FIG. 20A is a schematic pictorial illustration of a coupling mechanism for coupling a pressure conduit in pressure communication with arterial blood of an artery, in accordance with an embodiment of the present invention.
Figure 20B:
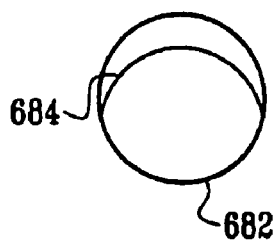
FIGS. 20B and 20C are schematic cross-sectional views of a coupling lumen of the coupling mechanism of FIG. 20A during systole and diastole, respectively, in accordance with an embodiment of the present invention.
Figure 20C:
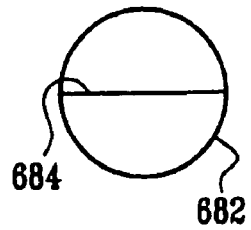

FIG. 20A is a schematic pictorial illustration of a coupling mechanism 680 for coupling pressure conduit 630 in pressure communication with arterial blood 647 of artery 645, in accordance with an embodiment of the present invention. FIGS. 20B and 20C are schematic cross-sectional views of a coupling lumen 682 of coupling mechanism 680 during systole and diastole, respectively, taken along line A-A of FIG. 20A, in accordance with an embodiment of the present invention. Coupling lumen 682 comprises a membrane 684 that isolates arterial blood 647 from pressure-transmitting fluid 633, while maintaining pressure communication between the blood and the pressure-transmitting fluid. During systole, the increased pressure of arterial blood 647 deflects membrane 684, as shown in FIG. 20B, thereby increasing the pressure of pressure-transmitting fluid 633. During diastole, the reduced pressure of arterial blood 647 allows membrane 684 to return to a neutral position, as shown in FIG. 20C. Alternatively or additionally, for some applications, pressure transfer techniques are used that are described in the above-mentioned US Patent Application Publication 2002/0103413 to Bugge et al., e.g., with reference to FIGS. 24, 25, and/or 26 thereof.

Figure 21:
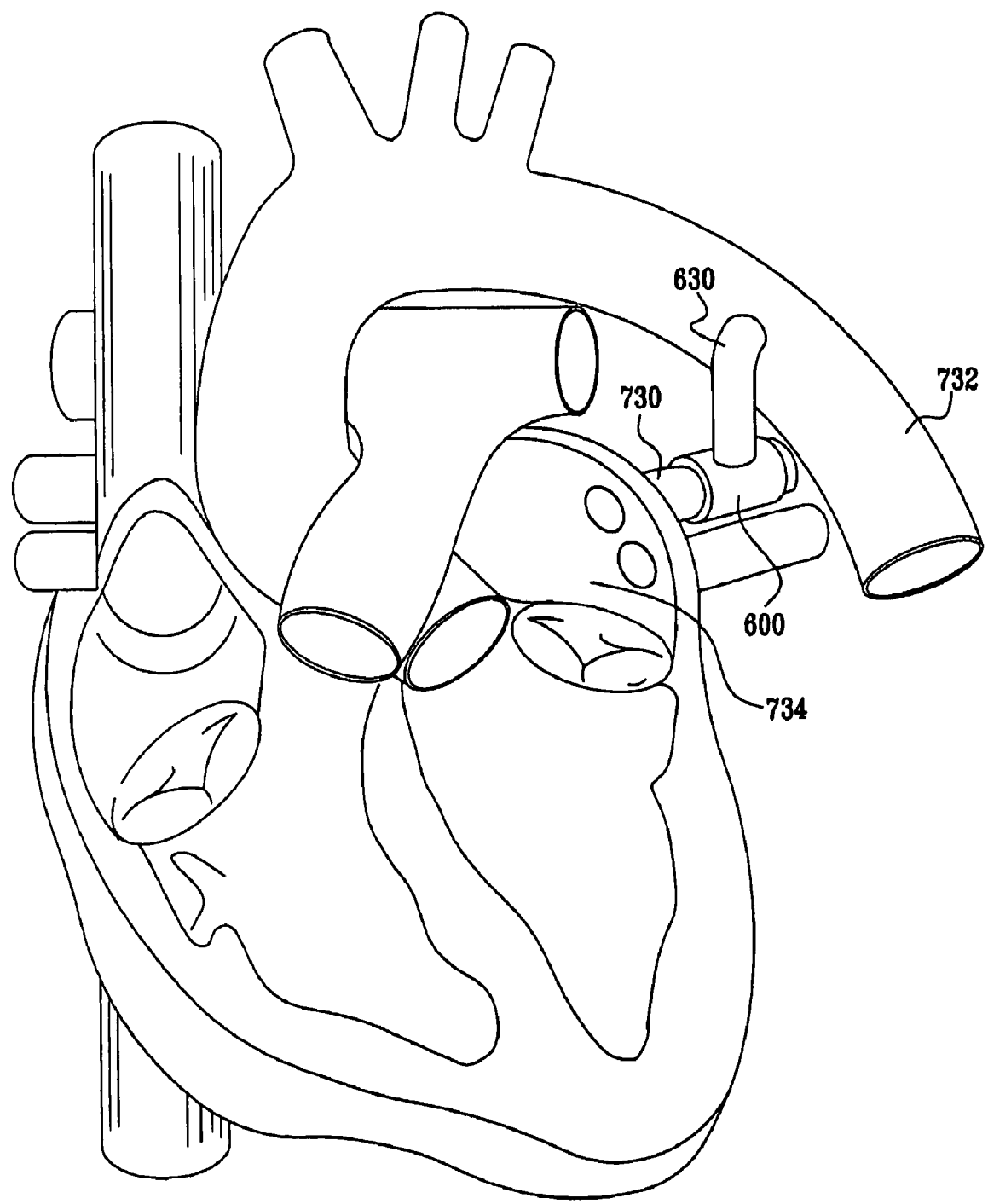
FIG. 21 is a schematic pictorial illustration of the use of the device of FIGS. 18A and 18B coupled to a pulmonary vein and a descending thoracic aorta of a subject, in accordance with an embodiment of the present invention.

FIG. 21 is a schematic pictorial illustration of the use of device 600 coupled to a pulmonary vein 730 and a descending thoracic aorta 732 of a subject, in accordance with an embodiment of the present invention. In this embodiment, blood vessel 640 includes pulmonary vein 730, and artery 645 includes descending thoracic aorta 732. Pressure conduit 630 is shown directly coupled to aorta 732, e.g., by anastomosis. Alternatively, pressure conduit 630 is coupled to aorta 732 using pressure-transfer techniques such as those described hereinabove with reference to FIGS. 20A, 20B, and 20C (configuration not shown). Device 600 increases blood flow from one or both of the lungs to a left atrium 734, thereby treating, for example, diastolic heart failure. For some applications, a plurality of devices 600 are coupled to a plurality of pulmonary veins 730 of the subject.

Figure 22:
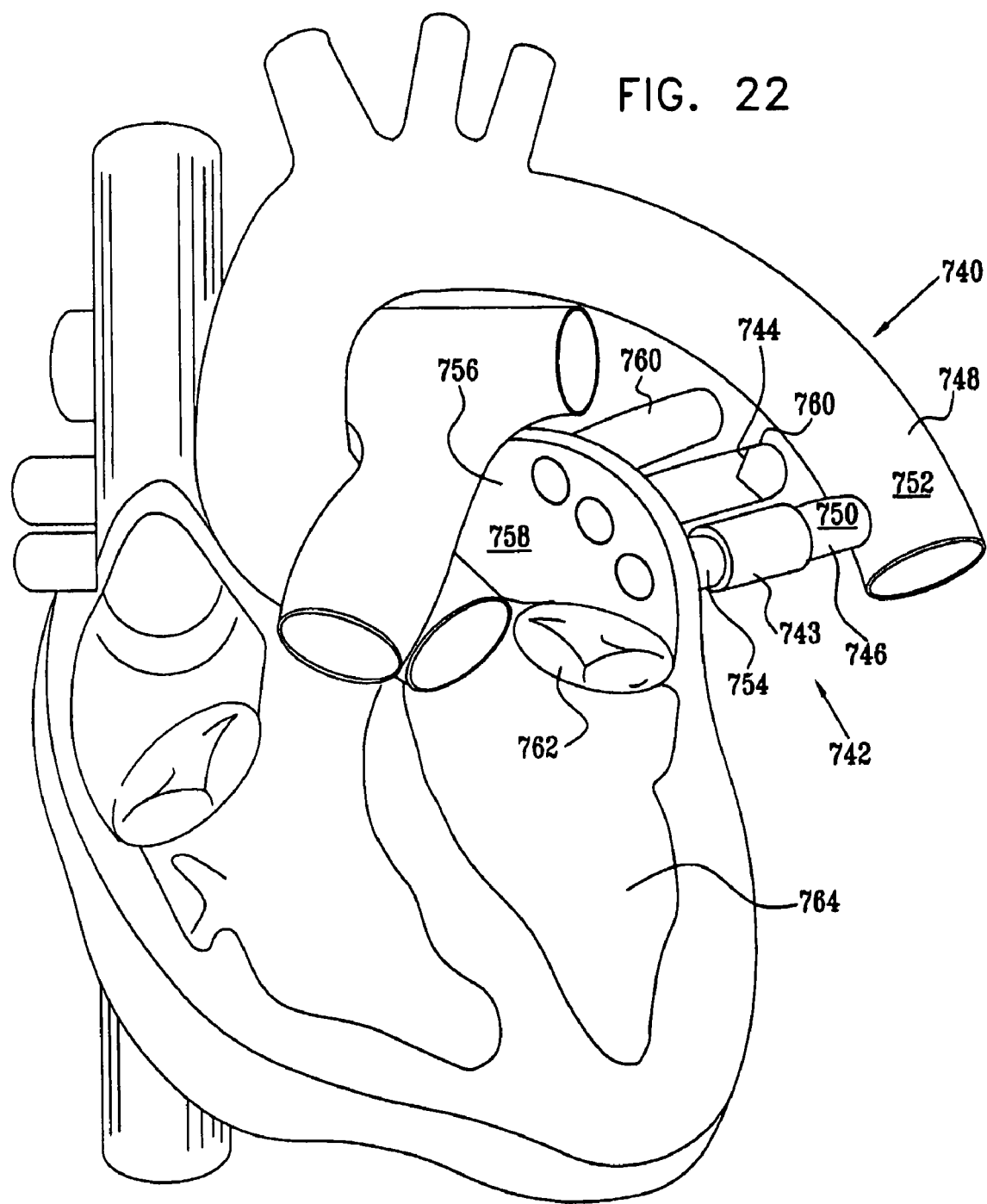
FIG. 22 is a schematic illustration of a diastolic heart failure treatment system, in accordance with an embodiment of the present invention.

FIG. 22 is a schematic illustration of a diastolic heart failure treatment system 740, in accordance with an embodiment of the present invention. System 740 comprises a blood flow regulation device 742, and, typically, one or more pressure-sensitive unidirectional valves 744. Each of valves 744 is implanted in one of pulmonary veins 760. The valves are configured to substantially prevent backflow of blood from pulmonary veins 760 to the lungs.

Blood flow regulation device 742 comprises a regulation unit 743, as described hereinbelow. Device 742 also comprises a pressure conduit 746, coupled to regulation unit 743. Pressure conduit 746 is adapted to be coupled to a descending thoracic aorta 748 of a subject, such that a pressure-transmitting fluid 750 is in pressure communication with blood 752 of aorta 748. For some applications, as shown in FIG. 22, pressure conduit 746 is coupled to aorta 748, e.g., by anastomosis, such that the interior of the conduit is in fluid communication with arterial blood 752; in these applications arterial blood 752 serves as pressure-transmitting fluid 750. For other applications, a membrane or other pressure-transfer mechanism separates the interior of pressure conduit 746 from arterial blood 752, for example using techniques such as described hereinabove with reference to FIGS. 20A, 20B, and 20C. In these applications pressure-transmitting fluid 750 typically comprises a biocompatible fluid, such as saline solution.

Device 742 further comprises a atrial conduit 754, coupled to regulation unit 743. Atrial conduit 754 is adapted to be coupled to a left atrium 756 of the subject, such that atrial blood 758 is in fluid communication with regulation unit 743 via atrial conduit 754.

Regulation unit 743 is configured to utilize the increased blood pressure of aortic blood 752 during systole to suck atrial blood 758 from left atrium 756 into regulation unit 743. Several configurations of regulation unit 743 for achieving this sucking are described hereinbelow with reference to FIGS. 23A, 23B, 24A, 24B, 25A, and 25B, and other configurations utilizing the same principles will be evident to those skilled in the art, having read the present application. The sucking of atrial blood 758 from left atrium 756 lowers the blood pressure in left atrium 756, thereby increasing blood flow from pulmonary veins 760 into the left atrium. This increased blood flow reduces backing up of blood in the lungs, and serves to treat, for example, diastolic heart failure.

During diastole, the pressure of aortic blood 752 drops, ejecting atrial blood 758 from regulation unit 743 into left atrium 756. The resulting increased blood pressure in the left atrium increases blood flow across a mitral valve 762 (which is open during diastole) into a left ventricle 764. In embodiments in which system 740 comprises valves 744, valves 744 close during diastole, preventing backflow to the lungs, and increasing blood flow across the open mitral valve. This increased blood flow further serves to treat, for example, diastolic heart failure.

Figure 23A:
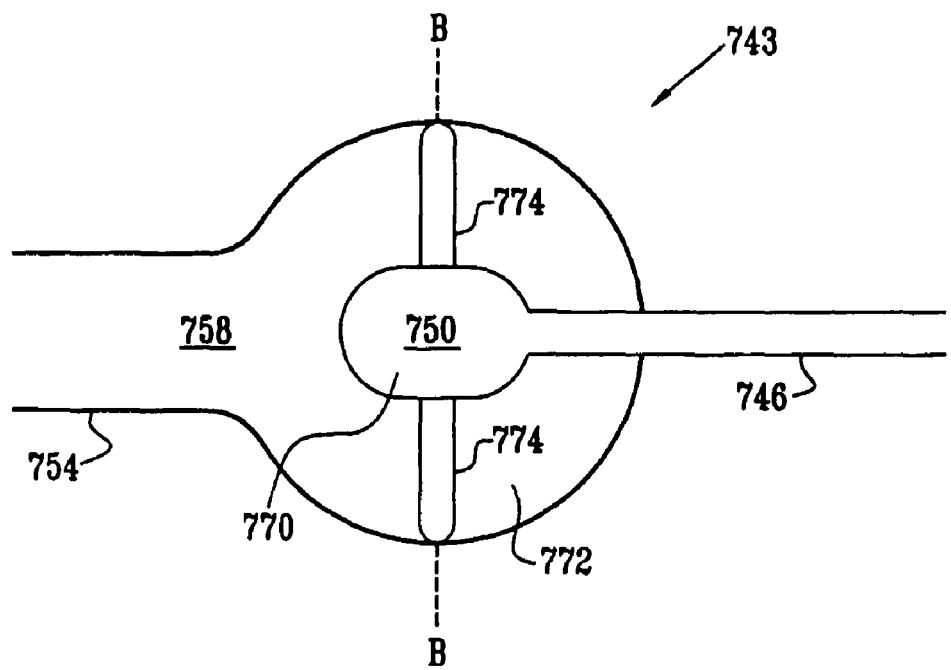
FIGS. 23A and 23B are schematic cross-sectional views of a configuration of a regulation unit of the system of FIG. 22, in accordance with an embodiment of the present invention.
Figure 23B:
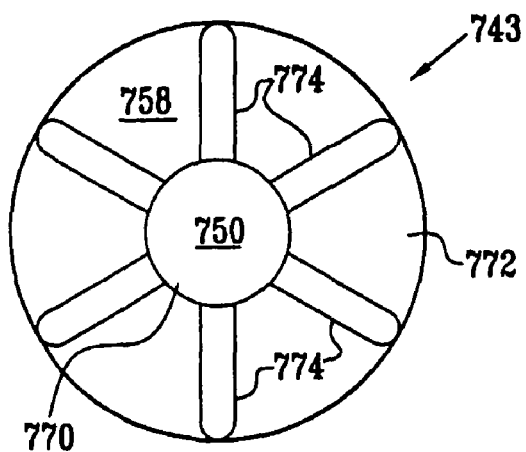

FIG. 23A is a schematic cross-sectional view of a configuration of regulation unit 743, and FIG. 23B is a schematic cross-sectional view of the configuration taken along line B-B of FIG. 23A, in accordance with an embodiment of the present invention. In this configuration, regulation unit 743 comprises a flexible, but not necessarily elastic, inner chamber 770, surrounded by an elastic outer chamber 772. Alternatively, outer chamber 772 is not necessarily elastic, and a spring (e.g., a band) external to the outer chamber is positioned to provide elasticity to the outer chamber (configuration not shown).

Inner chamber 770 is in fluid communication with pressure conduit 746, and contains pressure-transmitting fluid 750. Outer chamber 772 is in fluid communication with atrial conduit 754, and contains atrial blood 758. Regulation unit 743 comprises one or more substantially rigid members 774, coupled to inner chamber 770, and typically arranged radially outward from the inner chamber. Members 774 contact the inner surface of outer chamber 772.

Figure 24A:
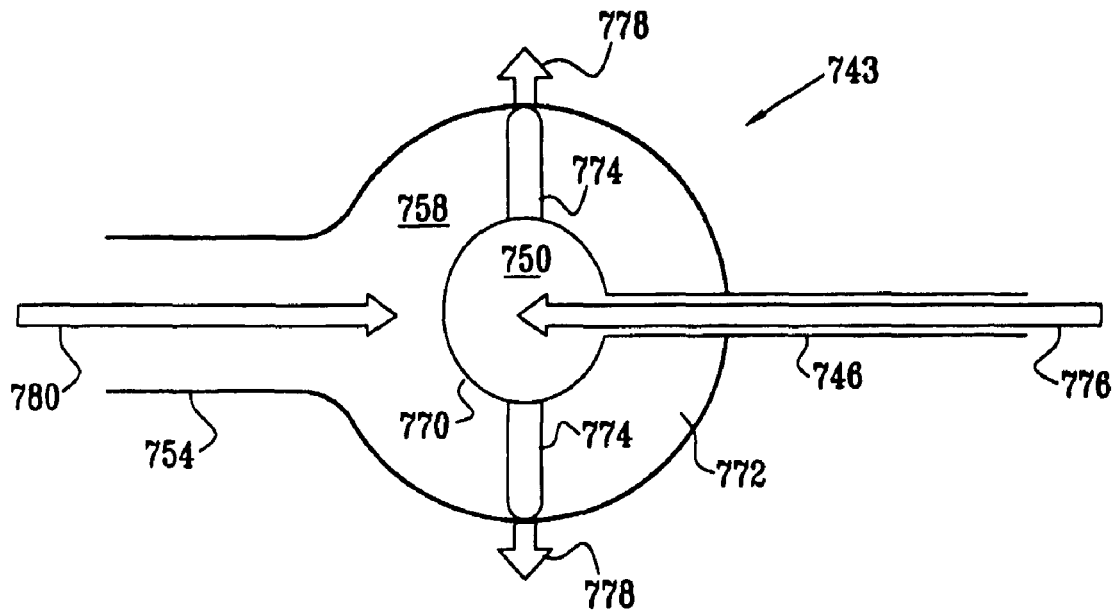
FIGS. 24A and 24B are schematic cross-sectional views of the regulation unit of FIGS. 23A and 23B during systole and diastole, respectively, in accordance with an embodiment of the present invention.
Figure 24B:
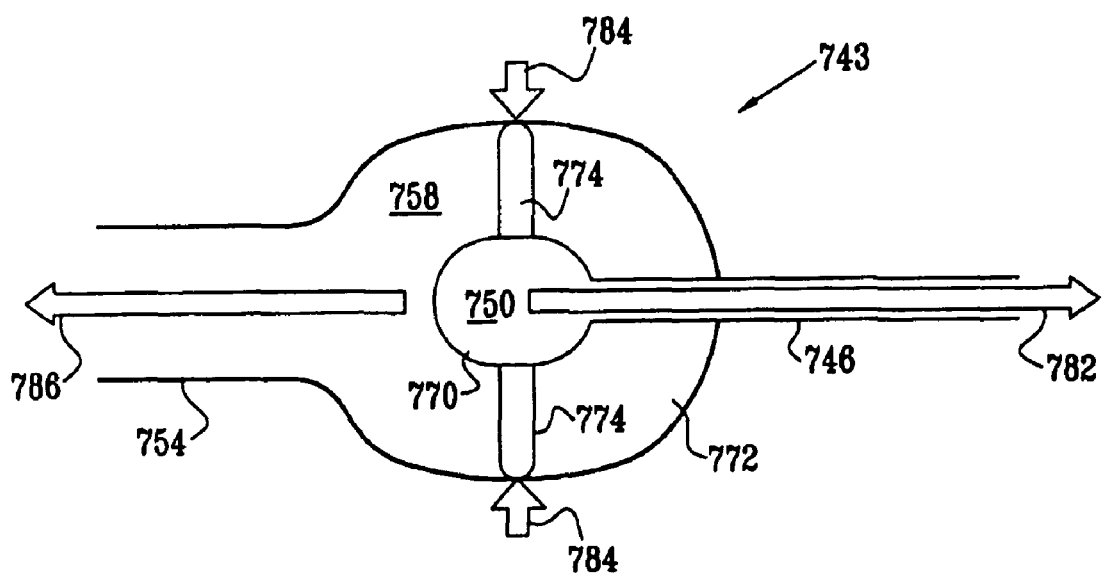

FIGS. 24A and 24B are schematic cross-sectional views of regulation unit 743 during systole and diastole, respectively, in accordance with an embodiment of the present invention. During a systolic phase of operation of regulation unit 743, as shown in FIG. 24A, the increased systolic blood pressure in aorta 748 (FIG. 22) is translated into increased pressure of pressure-transmitting fluid 750. Additional pressure-transmitting fluid 750 enters inner chamber 770, as symbolically represented by an arrow 776. The additional fluid expands inner chamber 770, pushing members 774 in the direction indicated by arrows 778. Members 774 push against the inner surface of outer chamber 772, causing the outer chamber to expand in the direction indicated by arrows 778, thereby storing potential energy in the elastic surface of the outer chamber. The increased volume of the outer chamber sucks additional atrial blood 758 into the outer chamber from left atrium 756 (FIG. 22) via atrial conduit 754, as symbolically indicated by an arrow 780.

During a subsequent diastolic phase of operation, as shown in FIG. 24B, the decreased diastolic blood pressure in aorta 748 (FIG. 22) is translated into decreased pressure of pressure-transmitting fluid 750. Pressure-transmitting fluid 750 exits inner chamber 770, as symbolically represented by an arrow 782. The resulting contraction of inner chamber 770 reduces the force applied to members 774 by inner chamber 770. The elastic surface of outer chamber 772 converts the stored potential energy to kinetic energy, thereby contracting outer chamber 772 in the direction indicated by arrows 784. As a result, atrial blood 758 is expelled from outer chamber 772 into left atrium 756 (FIG. 22) via atrial conduit 754, as symbolically indicated by an arrow 786.

Figure 25A:
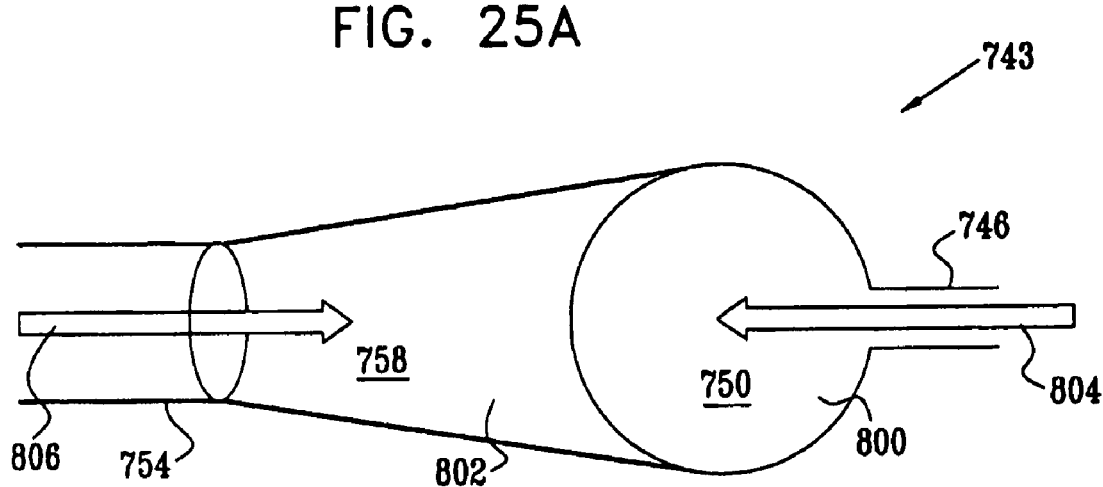
FIGS. 25A and 25B are schematic cross-sectional views of another configuration of the regulation unit of the system of FIG. 22, during systole and diastole, respectively, in accordance with an embodiment of the present invention.
Figure 25B:
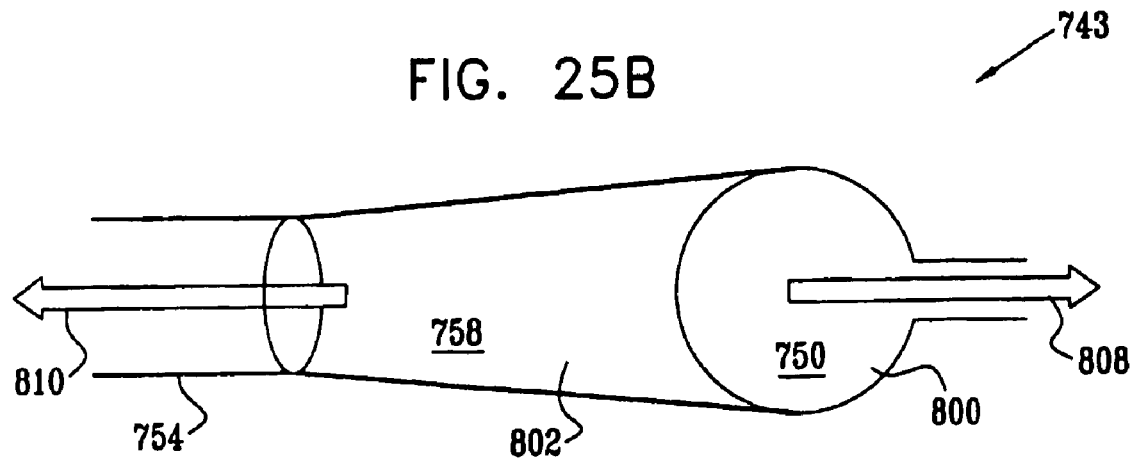

FIGS. 25A and 25B are schematic cross-sectional views of another configuration of regulation unit 743, during systole and diastole, respectively, in accordance with an embodiment of the present invention. In this configuration, regulation unit 743 comprises a flexible first chamber 800, in mechanical communication with a second flexible chamber 802. First chamber 800 is in fluid communication with pressure conduit 746, and contains pressure-transmitting fluid 750. Second chamber 802 is in fluid communication with atrial conduit 754, and contains atrial blood 758.

During a systolic phase of operation of regulation unit 743, as shown in FIG. 25A, the increased systolic blood pressure in aorta 748 (FIG. 22) is translated into increased pressure of pressure-transmitting fluid 750. Additional pressure-transmitting fluid 750 enters first chamber 800, as symbolically represented by an arrow 804. The additional fluid expands first chamber 800, thereby increasing the volume of second chamber 802. The increased volume of second chamber 802 lowers the pressure therein, sucking additional atrial blood 758 into the second chamber from left atrium 756 (FIG. 22) via atrial conduit 754, as symbolically indicated by an arrow 806.

During a subsequent diastolic phase of operation, as shown in FIG. 25B, the decreased diastolic blood pressure in aorta 748 (FIG. 22) is translated into decreased pressure of pressure-transmitting fluid 750. Pressure-transmitting fluid 750 exits first chamber 800, as symbolically represented by an arrow 808. The resulting contraction of first chamber 800 reduces the volume of second chamber 802, expelling atrial blood 758 from second chamber 802 into left atrium 756 (FIG. 22) via atrial conduit 754, as symbolically indicated by an arrow 810.

Figure 26:
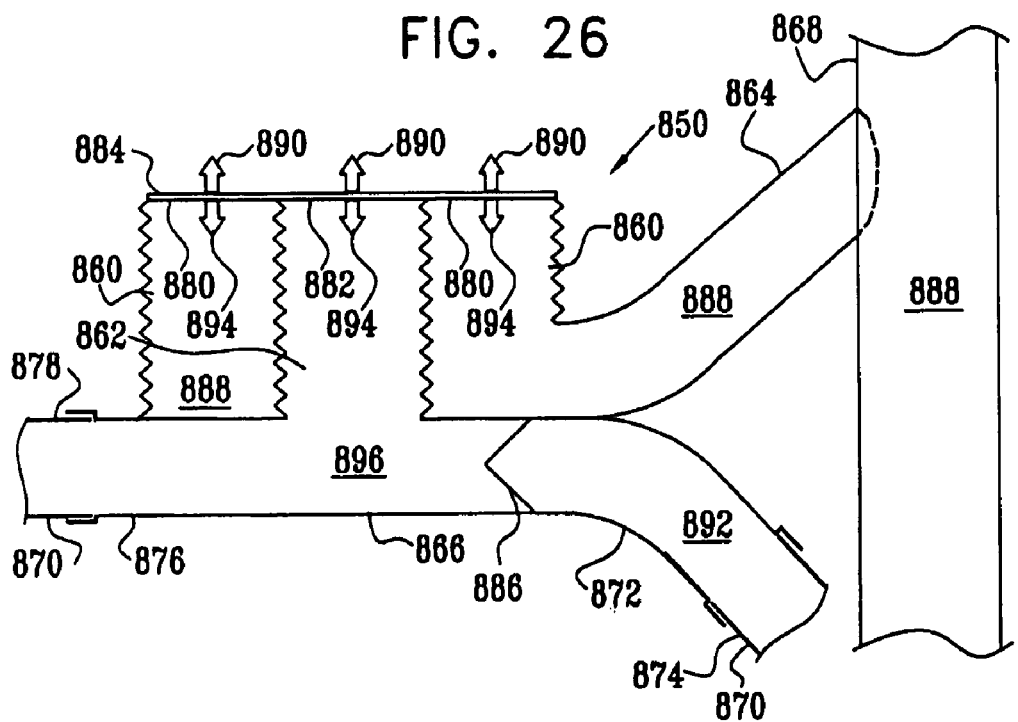
FIG. 26 is a schematic cross-sectional view of a still another blood flow amplification device, in accordance with an embodiment of the present invention.

FIG. 26 is a schematic cross-sectional view of a blood flow amplification device 850, in accordance with an embodiment of the present invention. Device 850 comprises a first flexible chamber 860, a second flexible chamber 862, an arterial conduit 864, and a venous conduit 866. Arterial conduit 864 is coupled to and in fluid communication with first chamber 860, and is adapted to be coupled to an artery 868 of a subject, such as by anastomosis. Venous conduit 866 is coupled to and in fluid communication with second chamber 862, and is adapted to coupled to a vein 870 of the subject, by coupling a proximal inflow end 872 of the conduit to a first site 874 of the vein, and a distal outflow end 876 of the conduit to a second site 878 of the vein, the second site distal to the first site with respect to blood circulation.

In the embodiment shown in FIG. 26, the chambers are generally cylindrically shaped, and second chamber 862 is shown surrounded by first chamber 860. Alternatively, the chambers have different shapes, and/or first chamber 860 and second chamber 862 are arranged side-by-side, or in another arrangement (configurations not shown).

First chamber 860 and second chamber 862 define a first surface 880 and a second surface 882, respectively, each of which surfaces is in mechanical communication with a common surface 884 that applies an elastically-derived force. For some applications, first surface 880 and second surface 882 together comprise surface 884. Surface 884 is adapted to facilitate storage, as potential energy, of the work applied thereto by first surface 880 and second surface 882, such as by using techniques described hereinabove with respect to surface 38, with reference to FIGS. 1A and 1B, and/or FIG. 2, mutatis mutandis.

Venous conduit 866 further comprises a pressure-sensitive valve 886, positioned upstream from second chamber 862. Valve 886 is typically in an open position only when a pressure gradient thereacross is greater than a threshold value, e.g., greater than between about 1 and about 4 mm Hg.

During a systolic phase of operation of device 850, arterial blood 888 from artery 868 enters first chamber 860. The blood applies systolic blood pressure to first surface 880, thereby expanding first chamber 860 and second chamber 862 in the direction indicated by arrows 890. First surface 880 applies force generated by the systolic blood pressure to surface 884, thereby storing potential energy in the source of the elastically-derived force. Also during at least a portion of systole, valve 886 opens and venous blood 892 flows through venous conduit 866 because of the natural pressure of the venous blood.

During a subsequent diastolic phase of operation, surface 884 converts the stored potential energy to kinetic energy, applying a force to both first surface 880 and second surface 882, thereby contracting first chamber 860 and second chamber 862 in the direction indicated by arrows 894. The increased pressure in second chamber 862 and venous conduit 866 causes valve 886 to close. The resistance to movement of venous blood 896 distal to valve 886 is substantially greater than the resistance to movement of diastolic arterial blood 888. In this configuration, during diastole, surface 884 applies a disproportionately large portion of the stored potential energy to second surface 882 of second chamber 862. The force applied to second chamber 862 generates a pressure in distal venous blood 896 that is greater than normal blood pressure in vein 870. As a result, device 850 drives distal venous blood 896 out of outflow end 876 at high pressure. Device 850 thus provides increased blood circulation in vein 870, thereby treating conditions caused by insufficient blood circulation in vein 870.

It is to be noted that the use of device 850 typically never brings arterial blood 888 and venous blood 892 into fluid communication with one another.

For some applications, device 850 is in pressure communication with arterial blood 888, but not fluid communication, for example using the techniques described hereinabove with reference to FIGS. 20A, 20B, and 20C, mutatis mutandis.

For some applications, device 850 comprises volume adjustment mechanism 80, as described hereinabove with reference to FIG. 4, mutatis mutandis. Alternatively or additionally, for some applications device 850 comprises pressure adjustment mechanism 90, as described hereinabove with reference to FIG. 5, mutatis mutandis (in which case slight mixing of arterial blood 888 and venous blood 892 does occur).

Figure 27:
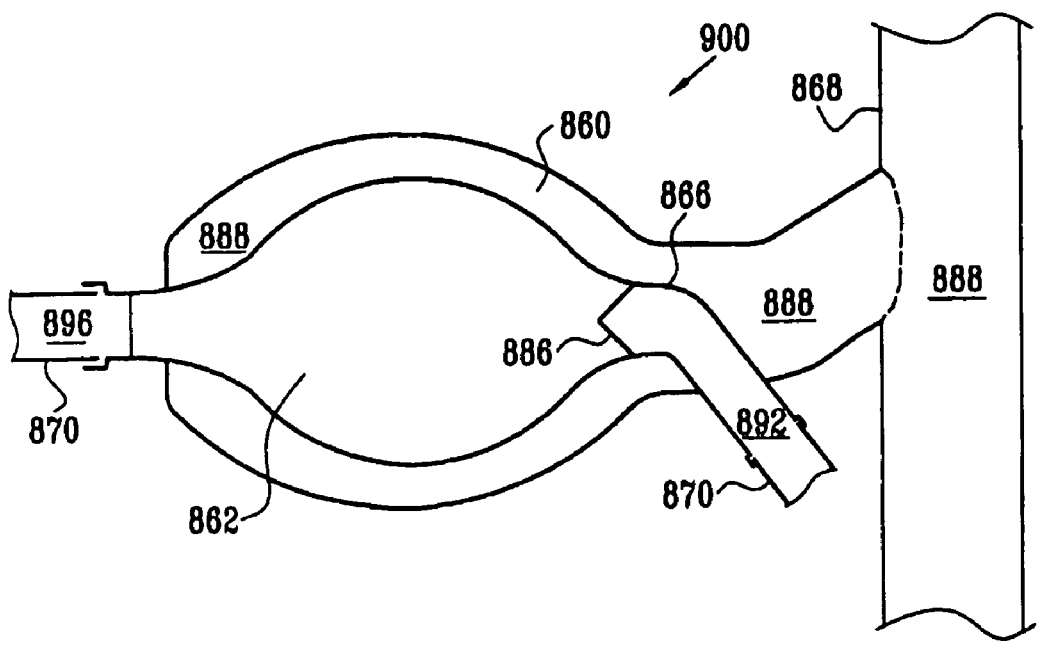
FIG. 27 is a schematic cross-sectional illustration of another blood flow amplification device, in accordance with an embodiment of the present invention.

FIG. 27 is a schematic cross-sectional illustration of a blood flow amplification device 900, in accordance with an embodiment of the present invention. Device 900 operates generally according to the principles of device 850, and the reference numbers in FIG. 27 refer to the same or similar structure as those in FIG. 26. Device 900 also employs some of the techniques of device 110, described hereinabove with reference to FIG. 6, mutatis mutandis.

It is to be understood that whereas embodiments of the present invention are described hereinabove with respect to controlling blood flow by use of a valve that opens and closes in response to pressure changes, the scope of the present invention includes the use of valve means having substantially no moving parts, but which bias flow in a predetermined direction by virtue of the shape of the valve means.

It is further to be understood that whereas embodiments of the present invention are described hereinabove with respect to generating pressure differentials by use of surfaces having different cross-sectional areas, the scope of the present invention includes the use of gears and other mechanical means for generating such pressure differentials.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising:
a first chamber and a second chamber, adapted to be in fluid communication with a first volume and a second volume of oxygenated blood of a subject, respectively, the first chamber and the second chamber having a first surface and a second surface, respectively;
a third surface adapted to apply an elastically-derived force, at least a first portion of the third surface in mechanical communication with the first surface, and at least a second portion of the third surface in mechanical communication with the second surface during at least a portion of a cardiac cycle; and
a pressure-sensitive valve coupled between the first chamber and the second chamber, the valve adapted to:
be in an open position during at least a portion of systole, such that the first chamber is in fluid communication with the second chamber and the first volume is in fluid communication with the second volume, and
be in a substantially closed position during diastole, such that the first chamber is substantially not in fluid communication with the second chamber and the first volume is substantially not in fluid communication with the second volume.

2. The apparatus according to claim 1, wherein the apparatus is adapted to expel, during diastole, oxygenated blood having a blood pressure greater than systolic blood pressure in a vicinity of the apparatus.

3. The apparatus according to claim 1, wherein the first chamber comprises:
a first sub-chamber, adapted to be in fluid communication with the first volume, and coupled to the valve; and
a second sub-chamber, having the first surface, wherein the first sub-chamber and the second sub-chamber are shaped so as to define an opening therebetween.

4. The apparatus according to claim 1, wherein the second chamber comprises:
a first sub-chamber, adapted to be in fluid communication with the second volume, and coupled to the valve; and
a second sub-chamber, having the second surface, wherein the first sub-chamber and the second sub-chamber are shaped so as to define an opening therebetween.

5. The apparatus according to claim 1, wherein the first surface and the second surface are adapted to apply respective forces to the third surface during systole, causing the third surface to store the forces as potential energy, and wherein the third surface is adapted to apply, during diastole, more of the stored potential energy to the second surface than to the first surface.

6. The apparatus according to claim 1, comprising at least one spring, configured to provide the elastically-derived force.

7. The apparatus according to claim 1, wherein the third surface comprises an elastic material, adapted to provide the elastically-derived force.

8. The apparatus according to claim 1, wherein the first surface comprises the third surface.

9. The apparatus according to claim 1, wherein the first surface and the second surface together comprise the third surface.

10. The apparatus according to claim 1,
wherein the first chamber is shaped so as to define a first opening between the first chamber and the first volume of blood,
wherein the second chamber is shaped to as to define a second opening between the second chamber and the second volume of blood, and
wherein the second opening has a diameter less than a diameter of the first opening.

11. The apparatus according to claim 1, wherein the apparatus is adapted to be coupled to an artery of the subject selected from the list consisting of: a penile artery of the subject and a dorsal penile artery of the subject.

12. The apparatus according to claim 1, wherein the apparatus is adapted to be coupled to a coronary artery of the subject.

13. The apparatus according to claim 1, wherein the first chamber and the second chamber are substantially radially symmetrical around a common longitudinal axis of the first chamber and the second chamber.

14. The apparatus according to claim 1, wherein the first surface has a first surface area, and wherein the second surface has a second surface area less than the first surface area.

15. The apparatus according to claim 1, comprising a tube, coupled to the second chamber, wherein the first chamber is adapted to be coupled to a first artery of the subject containing the first volume of oxygenated blood, and wherein the tube is adapted to be coupled to a second artery of the subject containing the second volume of oxygenated blood.

* * * * *